(12) United States Patent
Denney

(10) Patent No.: US 11,493,498 B2
(45) Date of Patent: *Nov. 8, 2022

(54) ASSAYS AND METHODS FOR DIAGNOSING SUBSTANCE USE DISORDER

(71) Applicant: VISION DIAGNOSTICS, INC., Branford, FL (US)

(72) Inventor: Jerry W. Denney, Branford, FL (US)

(73) Assignee: VISION DIAGNOSTICS, INC., Branford, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/570,413

(22) Filed: Jan. 7, 2022

(65) Prior Publication Data
US 2022/0128540 A1 Apr. 28, 2022

Related U.S. Application Data

(63) Continuation of application No. 16/226,768, filed on Dec. 20, 2018.

(51) Int. Cl.
| | |
|---|---|
| *G01N 33/487* | (2006.01) |
| *G01N 33/493* | (2006.01) |
| *G01N 33/52* | (2006.01) |
| *G01N 33/537* | (2006.01) |
| *G01N 33/539* | (2006.01) |

(52) U.S. Cl.
CPC ..... *G01N 33/48714* (2013.01); *G01N 33/493* (2013.01); *G01N 33/526* (2013.01); *G01N 33/539* (2013.01); *G01N 33/5375* (2013.01); *G01N 2458/00* (2013.01); *G01N 2560/00* (2013.01); *G01N 2800/307* (2013.01)

(58) Field of Classification Search
CPC ........... G01N 33/48714; G01N 33/493; G01N 33/526; G01N 33/5365; G01N 33/539; G01N 2458/00; G01N 2560/00; G01N 2800/307
See application file for complete search history.

(56) References Cited

U.S. PATENT DOCUMENTS

| | | | |
|---|---|---|---|
| 5,057,435 A | 10/1991 | Denney | |
| 5,753,451 A | 5/1998 | Smith | |
| 5,981,206 A | 11/1999 | Arter et al. | |
| 10,082,495 B2 | 9/2018 | Denney | |
| 10,571,457 B2 | 2/2020 | Denney | |
| 2008/0286881 A1 | 11/2008 | Apel et al. | |
| 2011/0118141 A1 | 5/2011 | Pugia | |
| 2017/0010276 A1 | 1/2017 | Chen et al. | |
| 2017/0269058 A1 | 9/2017 | Denney | |
| 2018/0127799 A1 | 5/2018 | Denney | |

FOREIGN PATENT DOCUMENTS

WO    WO 2015/130225    9/2015

OTHER PUBLICATIONS

Daniel, O. et al., "Urinary Excretion of Acid Phosphastase," *British Medical Journal*, Jan. 2, 1954, pp. 19-21.
Gault, M.H. et al., "Clinical Significance of Urinary LDH, Alkaline Phosphatase and Other Enzymes," *Canad. Med. Ass. J.*, 1969; pp. 208-215, vol. 101.
Guo, W. et al., "DNA Verified Sample Authenticity for Urine Drug Testing Results from early commercial experience with a new method for matching submitted urine samples to specific patients," Postgraduate Medicine, 2016, pp. 35-36, vol. 128, No. S2.
Samilpa, P. et al., "Synthetic Urine How Easy is it to find, order and have synthetic urine delivered," Postgraduate Medicine, 2016, pp. 78-79, vol. 128, No. S2.
Combating cheating in urine drug testing, [online, webpage, retrieved Sep. 11, 2018] from: https://blog.employersolutions.com/combatting-cheating-in-urine-drug-testing/, p. 1.
Needleman, S. B. et al. "Creatinine Analysis in a Single Collection Urine Specimens" *Journal of Forensic Science*, 1992, pp. 1125-1133, vol. 37.

*Primary Examiner* — Christopher Adam Hixson
(74) *Attorney, Agent, or Firm* — Saliwanchik, Lloyd & Eisenschenk

(57) ABSTRACT

Assays and methods for verifying the validity of a urine sample submitted for Drugs of Abuse (DOA) testing. Embodiments include a SUD Diagnostic Panel that includes six assays: specific gravity index assay, long-duration counterfeit urine assay, short-duration counterfeit urine assay, oxidant history assay, pH assay, and creatinine assay. The SUD Diagnostic Panel detects twelve principle classes of adulteration. Detection of adulteration of one or more urine samples from a patient indicates an attempt to subvert test results and provides an objective indication in one instance and an object diagnosis in another instance of SUD.

22 Claims, 11 Drawing Sheets
(6 of 11 Drawing Sheet(s) Filed in Color)

| ADULTERANT | Specific Gravity INDEX (SGI) | % ABOVE 0.035 CUTOFF |
|---|---|---|
| UNADULTERATED | | |
| Potassium Nitrite (Klear) | 0.019 | 0% |
| Liquid-Plumr® | 0.019 | 0% |
| Baking Soda | 0.019 | 0% |
| Table Salt | 0.019 | 0% |
| ADULTERATED 1% W/V | | |
| Potassium Nitrite (Klear) | 0.385 | 10% |
| Liquid-Plumr® | 0.517 | 48% |
| Baking Soda | 0.637 | 82% |
| Table Salt | 0.643 | 84% |
| ADULTERATED 5% W/V | | |
| Potassium Nitrite (Klear) | 0.0590 | 186% |
| Liquid-Plumr® | 0.844 | 1,263% |
| Baking Soda | 0.1081 | 2,239% |
| Table Salt | 0.1087 | 2,288% |

FIG. 11

ASSAYS AND METHODS FOR DIAGNOSING SUBSTANCE USE DISORDER

CROSS-REFERENCE TO RELATED APPLICATION

This application is a continuation of U.S. application Ser. No. 16/226,768, filed Dec. 20, 2018, now allowed.

BACKGROUND OF INVENTION

Substance use disorder (SUD) is a condition in which a patient exhibits a pathologic pattern of behavior of continued use of a substance despite experiencing significant negative consequences related to such use. Manifestations of SUD include impaired control of use, social impairment, risky use behavior, and efforts to hide use. There may also be physiological manifestations such as changes in brain function.

The substance drugs of abuse (DOA) utilized by those suffering with SUD are typically those that are subject to subversion techniques. Teenage children are a particularly vulnerable class. Overdose deaths in this class exceed deaths from school shootings and other cases of death combined. Unfortunately, parents and teachers have only behavioral observations to question if an individual has SUD. But, these same observations could result from other psychiatric or behavioral problems. The internet and other social media provide a plethora of information about how to subvert or "beat" a drug test and subversion products can be easily obtained. For this reason, neither parents nor teachers or physicians cannot rely upon current drug screening for diagnosis. Worse, negative drug results lead to the belief that symptoms are caused by other factors and treatment is not undertaken. This problem is not limited to teenagers. The overall detection of DOA has been seriously compromised due to the wide use of subversion agents and the success of these agents in masking detection. Thus, the metric data relied on to determine the targeting means used to combat the current opioid crisis is seriously flawed. These flaws in the data that is relied on degrade the effectiveness of providing treatment and recovery services and correspondingly adds greatly to the national costs related to drug use and abuse.

There are currently twelve recognized principle classes of subversion, which are used to adulterate or substitute for a patient's urine sample: (1) Alteration of pH, (2) simple dilution either in vivo or in vitro, (3) in vivo dilution with creatine/protein/water loading, (4) salting (e.g., baking soda), (5) oxidant adulteration (e.g., Stealth™), (6) gluteraldehyde adulteration, (7) heavy metal adulteration, (e.g. zinc) (8) substitution with synthetic (Counterfeit) urine, (9) substitute with urine from another person, (10) sulfhydryl blocking agents, (e.g., iodoacetamide) (11) cationic detergents, (e.g., dimethylbenzylalconium chloride), and (12) proteases, (e.g., bromelain).

Laboratories typically screen samples for DOA with automated equipment, such as clinical analyzers, using commercially available Enzyme Immunoassays (EIA) and related methods and reagents. Current screening methods utilize bodily fluid or hair to detect the presence of a drug in the urine and may attempt to assess the validity (absence of subversion) of the sample by measuring or detecting pH, creatinine, reflex specific gravity, and general oxidant use. Nonetheless, the positivity rate for workplace drug testing has been steadily declining for the last decade. During the same period, deaths from drug overdoses have steadily increased. This indicates that the current testing protocols are failing. Without the ability to test the validity of a sample, proceeding directly to a test for the presence of a drug can result in inaccurate results. For example, it has been shown that the current assays and methods used for screening samples are effective only for detecting the first two classes of subversion, which represents less than 20% of total subversion efforts and that percentage is declining.

There has been increased evidence and better understanding of the biological processes that underlie compulsive drug use. This has resulted in SUD being recognized as a medical illness, opening the door to numerous forms of treatment that can now be used to help patients. However, as with many diseases, it is important that the diagnosis of SUD be made early as the disease becomes more difficult to treat as the brain chemistry of the SUD victim changes. Too often the diagnosis is established only after the first overdose. This is the equivalent of diagnosing diabetes only after the diabetic suffers a diabetic coma. Combatting the problem must first start with more effective screening for drug use so that SUD can be identified.

It is also important that improved assays and methods used for screening be usable in automated equipment. This will provide a quicker and more cost effective method for conducting tests, ensuring their continued and frequent use.

BRIEF SUMMARY

The subject invention successfully addresses the disadvantages with the previously known drug use screening methods and provides certain attributes and advantages, which have not been possible by those known procedures. In particular, the subject invention provides novel, relatively inexpensive, and highly effective improvements to currently known screening assays. More specifically, the subject invention provides a screening panel capable of verifying sample validity by detecting use of one or more of the twelve recognized classes of drug use subversion techniques. The subject invention can also employ methods of use that improve the results of DOA testing protocols to more accurately diagnose SUD.

The screening panel includes six assays that, when used together, can detect all twelve of the recognized principle classes of subversion. The screening assay methods of the subject invention can be employed in advance of drug screening tests, to verify the validity of the sample before additional time and cost is spent conducting further tests. The screening method includes three assays that can measure the presence or absence of specific bio-markers in a urine sample, a specific gravity index assay that can measure the sodium and potassium in a urine sample, an improved creatinine assay, and an improved pH assay. These combined assays provide a screening panel and method, referred to herein as the "SUD Diagnostic Panel" the results of which can accurately determine if a urine sample has been adulterated by any of the twelve known classes of subversion techniques. In order for the SUD Diagnostic Panel to remain effective, it is important that all known means of subversion be detectable. If, for example, only a Counterfeit urine assay is added due to its currently common use, the internet and social media will rapidly report that drug users are being "busted" for using counterfeit urine and will recommend other subversion means. This will render the Counterfeit urine assay obsolete in the absence of other assay techniques.

Advantageously, embodiments of the assays used in the SUD Diagnostic Panel are capable of being utilized in standard laboratory automation equipment, such as chemical analyzers typically used to facilitate automated urine sample analysis. Specifically, spectrophotometry and LC/MS analyses of a sample treated with the assay embodiments of the subject invention can be used to indicate whether a sample contains or has contained an adulterant or has otherwise been subjected to adulteration or substitution.

Attempted subversion of a drug test can be a manifestation of SUD and indicates a compelling need to continue use of the substance. An indication of subversion is thus an objective indication of a behavioral disorder indicative of SUD. Combating the problem of SUD should first start with the 6 assay "SUD Diagnostic Panel."

Specific methods of use of the SUD Diagnostic Panel with spectrophotometric and LC/MS protocols employed for DOA testing can ensure that such analyses are conducted on valid samples, thereby reducing unnecessary tests. Furthermore, failing any one of the 6 assays provides a provisional diagnosis of SUD. Confirmatory testing is then more accurate because passing the SUD panel will allow only valid samples to proceed to drug screening tests. Donors of failed SUD panel testing should be required to provide a new sample under the most secure collection means. That sample can then proceed to Liquid or Gas chromatography/Mass Spectrophotometry (LC/MS) testing for a broader range of drugs than available with EIA screening. Alternatively, the retaken sample can be subjected to the SUD Diagnostic Panel to ensure validity prior to proceeding with LC/MS testing.

BRIEF DESCRIPTION OF DRAWINGS

This patent or application file contains at least one drawing executed in color. Copies of this patent or patent application publication with color drawing(s) will be provided by the Office upon request and payment of the necessary fee.

In order that a more precise understanding of the above recited invention can be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings.

FIG. 11 shows the pH ranges and associated colors for the pH indicator dyes utilized with embodiments of the pH assay of the subject invention.

DETAILED DISCLOSURE

Figure 1A:
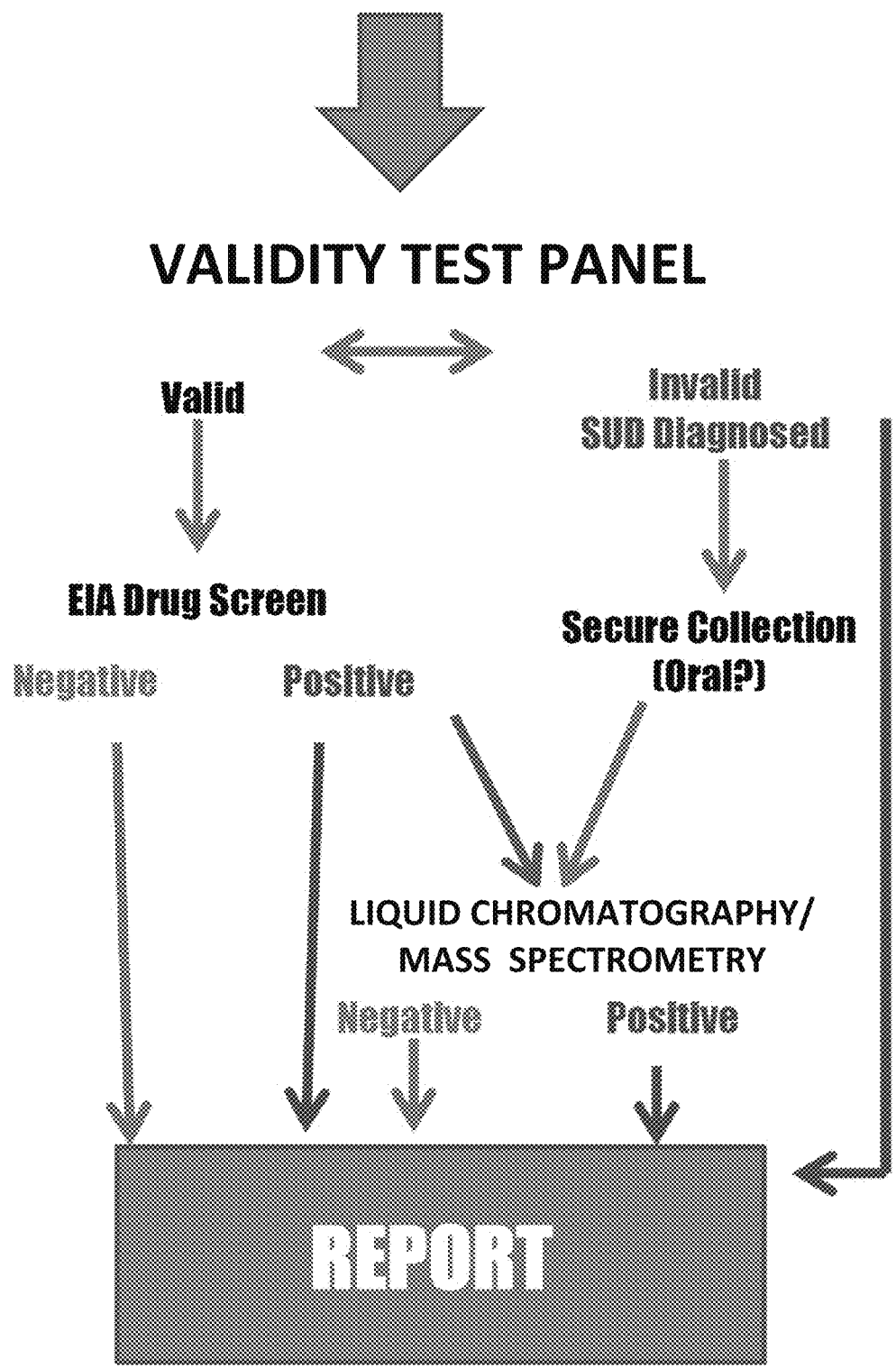
FIG. 1A is a flowchart illustrating a procedure by which an embodiment of a SUD Diagnostic Panel, according to the subject invention, can be used to detect an invalid and potentially adulterated urine sample and the various procedures that can be taken when the sample is determined to be valid and when the sample is determine to be invalid.

The subject invention pertains to an objective method of diagnosing Substance Abuse Disorder (SUD) utilizing an assay panel. More specifically, the subject invention provides one or more embodiments of a screening panel comprising six separate assays capable of detecting whether a urine sample has been adulterated or substituted by any of the twelve principle classes of subversion techniques. It has been shown that the use of subversion techniques is a manifestation of SUD. Thus, detection of subversive behavior can be indicative of SUD.

The following description will disclose that the subject invention is particularly useful in the field of urine analysis utilizing automated equipment, such as, chemical analyzers, to detect adulteration or substitution of a sample and use of Drugs of Abuse (DOA). A person with skill in the art will be able to recognize other uses that would be applicable to the devices and methods of the subject invention. For example, certain diseases or disease states may also be detectable with the embodiments of the subject invention. While the subject application describes, and many of the terms herein relate to, a use for detecting or diagnosing SUD, which is related to use of DOA, other uses and modifications apparent to a person with skill in the art and having benefit of the subject disclosure are contemplated to be within the scope of the present invention.

When the term "about" is used herein, in conjunction with a numerical value, it is understood that the value can be in a range of 95% of the value to 105% of the value, i.e. the value can be +/−5% of the stated value. For example, a temperature of 100° C. means from about 95° C. to about 105° C.

Substance Use Disorder (SUD) is a recognized mental disorder that manifests as behavioral characteristics related to use of Drugs of Abuse (DOA). More specifically, it has been shown that efforts to mask, hide, or otherwise subvert detection of use of DOA is indicative of SUD. In fact, the Substance Abuse and Mental Health Services Administration (SAMHSA) recognizes that behavior changes are a reason to suspect SUD. The ability to detect subversion of test results, usually by one of the twelve principle classes of subversion, can be an objective indication of a behavioral change indicative of SUD.

Urine sample analysis with automated equipment using spectrophotometric and LC/MS techniques is the most cost effective means for detecting DOA or their metabolites. The current assay panel used to analyze a urine sample relies on detecting the presence of a DOA in a urine sample. The current assays used for detecting invalidity of samples for DOA testing include analysis of pH, creatinine levels, specific gravity, and general oxidant detection. These assays are usually capable of effectively detecting only two of the twelve classes of subversion—adulteration by modifying pH and simple dilution. Thus, if any other subversion technique is used, the current assay panel can return a false negative result for DOA.

Embodiments of the subject invention provide an advantageous improvement to the current assay panel by replacing the current specific gravity and general oxidant assays with a new and more broadly effective Specific Gravity Index assay and an Oxidant History assay. Added to the current assay panel are two unique, highly effective Long Duration (LD) and Short Duration (SD) assays for detecting Counterfeit Urine. Also disclosed herein are improved pH and creatinine tests. The SUD Diagnostic Panel embodiments of the subject invention provide six assays capable of detecting all twelve of the recognized subversion techniques: Counterfeit (1) Alteration of pH, (2) simple dilution either in vivo or in vitro, (3) in vivo dilution with creatine/protein/water loading, (4) salting (e.g., baking soda), (5) oxidant adulteration (e.g., Stealth™), (6) gluteraldehyde adulteration, (7) heavy metal adulteration, (e.g., zinc), (8) substitution with synthetic (Counterfeit) urine (9) substitution with urine from another person, (10) sulfhydryl blocking agents, (e.g., iodoacetamide) (11) cationic detergents, (e.g., dimethylbenzylalconium chloride), and (12) proteases, (e.g., bromelain). Alternative embodiments can include fewer than the six assays. Utilization of the full six assay screening panel can, however, provide the most reliable objective diagnosis of SUD.

The following Table 1 lists the 12 currently known methods of adulteration, the assay useful in detecting such adulteration, and the conditions under which adulteration is confirmed, as described herein:

TABLE 1

Subversion Techniques and methods of detection

| Method of Adulteration or Substitution: | Assay for Detection: | Criteria for Confirmation: |
|---|---|---|
| Change of pH | pH Assay | pH less than 3 and greater than 11 |
| Simple dilution, in vivo or in vitro | Specific Gravity Index (SGI) Assay and Creatinine Assay | Creatinine < 20.0 and/or SGI < 1.0030 |
| In vivo dilution with creatine/protein/water loading | Specific Gravity Index (SGI) Assay | SGI < 1.0030 |
| Salting | Specific Gravity Index (SGI) Assay | SGI > 1.0350 |
| Oxidant | Oxidant History Assay | Uric Acid Equivalents < 10 |
| Gluteraldehyde | Specific Gravity Index (SGI) Assay and Long-Duration (LD) Assay | SGI < 1.0030 and LD < 8 |
| Heavy Metal | Specific Gravity Index (SGI) Assay | SGI < 1.0030 |
| Substitution with synthetic (Counterfeit) urine product | Long-Duration (LD) Assay and Short-Duration (SD)Assay | LD: Females < pH 9; Males < pH 12 SD: Females < pH 9 Males < pH 12 |
| Substitution with the urine of another person | Short-Duration (LD) Assay | SD: Females < pH 9; Males < pH 12 |
| Sulfhydryl blocking agents | Specific Gravity Index (SGI) Assay | SGI < 1.0030 |
| cationic detergents | Specific Gravity Index (SGI) Assay | SGI < 1.0030 |
| Protease | Specific Gravity Index (SGI) Assay | SGI < 1.0030 |

Figure 1B:
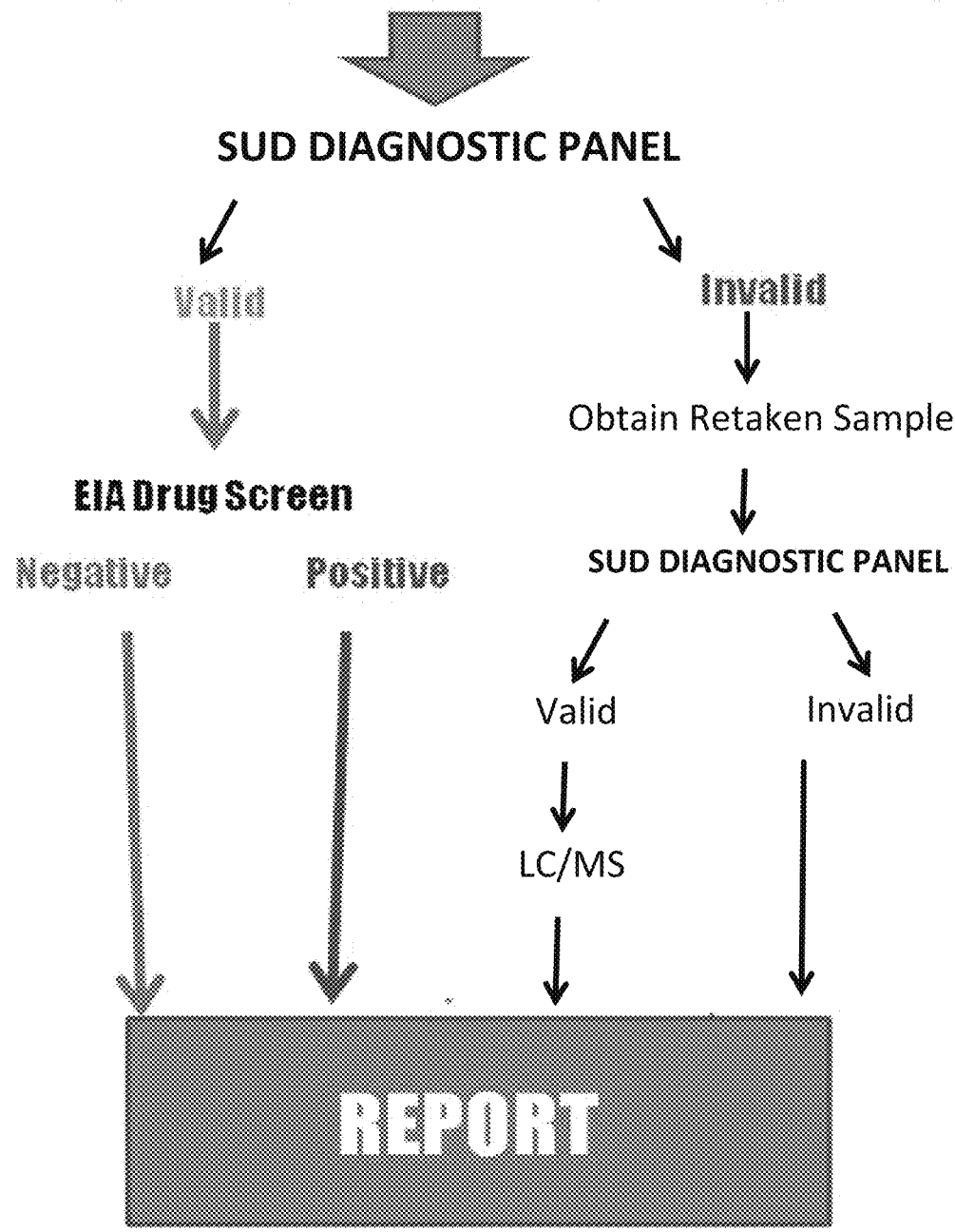
FIG. 1B is a flowchart illustrating an alternative procedure by which an embodiment of a SUD Diagnostic Panel, according to the subject invention, can be used to detect an invalid and potentially adulterated urine sample and used again on a retaken urine sample to detect whether it is invalid and also potentially adulterated.

As shown in FIG. 1, embodiments of a SUD Diagnostic Panel can be incorporated into the current methods for analyzing a urine sample after first testing whether a sample is valid, or if it has been subjected to adulteration or substitution. A SUD Diagnostic Panel can be conducted prior to any tests conducted for DOA or metabolites thereof If the SUD Diagnostic Panel indicates that the sample is valid, further testing by standard Enzyme Immunoassays (EIA) can be conducted and, because the urine sample was validated, the results can be considered accurate.

As discussed above, SUD is characterized by the patient taking steps to hide their use of DOA. Their reliance, a.k.a. addiction, to the DOA causes them to engage in risky behaviors, such as attempts to subvert DOA tests. In one embodiment, if the SUD Diagnostic Panel indicates that the sample is invalid, results can be an initial indication of SUD. At that point, steps can be taken to secure another sample under closer scrutiny.

In one embodiment, the retaken sample can be retested with the SUD Diagnostic panel to again determine if the retaken sample is valid or invalid. If the retaken sample is determined to be invalid, further testing can be avoided and an appropriate report provided. In one embodiment, an invalid retaken sample can be considered further objective indication of SUD. The use of adulteration techniques to subvert DOA tests can be considered a risky behavior. The reliability of the SUD Diagnostic Panel in detecting adulteration of urine samples can make it an important step in detecting such risky behavior. In an alternative embodiment, a SUD Diagnostic panel result that indicates an invalid retaken sample can be considered an objective diagnosis of SUD.

If the retaken test is determined to be valid, additional and more exact Liquid or Gas Chromatography/Mass Spectrophotometry (LC/MS) tests can be conducted to determine the presence of DOA. In one embodiment, a diagnosis of SUD can be objectively confirmed if the LC/MS tests indicate DOA in the retaken sample.

Unlike the enzyme immunoassay procedures (EIA), LC/MS procedures can detect a much wider spectrum of DOA. Thus, confirmation of DOA in a sample using LC/MS can be an important step in the objective diagnosis of SUD.

Many drugs are present in urine samples as glucuronide metabolites. It is known that detection of these glucuronide metabolites can be inexact and inaccurate with LC/MS procedures for several reasons. For the LC/MS procedure to be effective, the enzyme glucuronidase is used to hydrolyze the glucuronide metabolites to create a free form of a drug that may be present in the urine sample, which can then be detected by LC/MS procedures.

The inventor has discovered that the effectiveness of LC/MS procedures can be reduced when the sample is subjected to certain classes of subversion techniques listed in Table 1. Specifically, the glucuronidase enzyme activity is destroyed by heavy metal adulteration, such as with p-chloromercuriobenzoate (PCMB) and also with sulfhydral blockers, such as iodoacetamide (IAA). The use of these types of adulterants and their inactivation of the glucuronidase enzyme can adversely affect LC/MS procedures and results and reduce its effectiveness in confirming a diagnosis of SUD.

Figure 2:
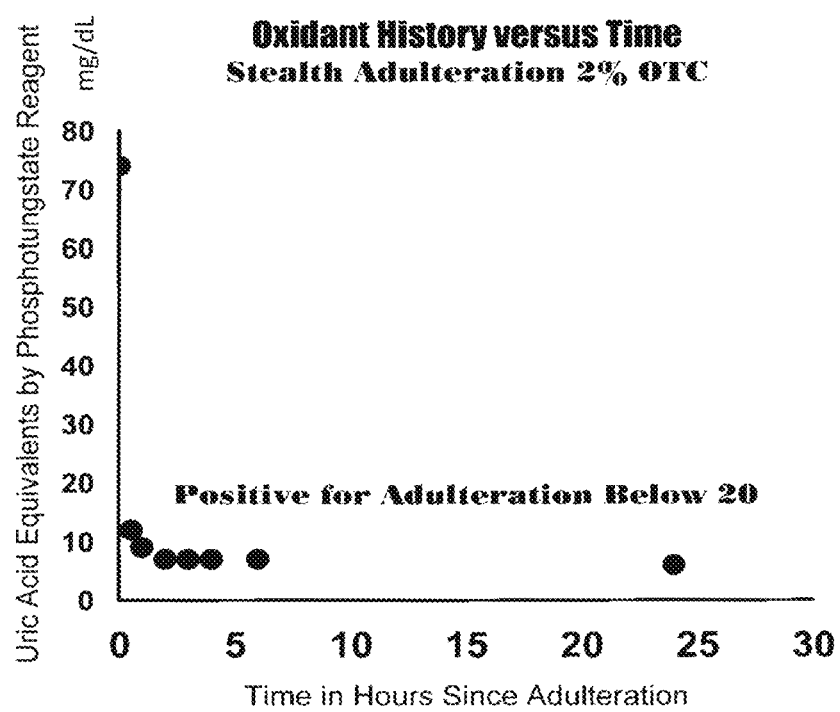
FIG. 2 is a graph of an Oxidant History obtained using the Uric Acid Equivalents in a urine sample that has been adulterated with STEALTH, a commercially-available adulterant.

The SUD Diagnostic Panel provides the advantageous ability to detect adulterants that can affect LC/MS procedures and results. FIG. 2 illustrates an example of a method for analysis of samples utilizing the SUD Diagnostic panel. In one embodiment, the SUD Diagnostic Panel is utilized to analyze a urine sample to determine validity. In a further embodiment, the SUD panel is utilized on retaken samples before conducting LC/MS DOA testing procedures. This can provide LC/MS results that can be relied on to diagnose SUD.

Utilization of the full SUD Diagnostic Panel, with all six assays, can most accurately indicate the use a subversion technique. The methods of using the SUD Diagnostic Panel with both initial and retaken urine samples can provide an effective means for objectively diagnosing SUD. Each of the assays in the SUD Diagnostic panel and their mode of operation are discussed in detail below.

I. Oxidant History Assay Utilizing Bio-Markers in Urine

Embodiments of an Oxidant History assay can be used alone or to create an Oxidant History (OHist), which utilizes two or more marker values to demonstrate historical changes in the sample markers during a pre-determined time window. U.S. Pat. No. 10,082,495 describes an Oxidant History Assay that can be utilized with embodiments of the screening panel of the subject invention. The entirety of U.S. Pat. No. 10,082,495 is hereby incorporated by reference.

Advantageously, the results obtained with an OHist can be unaffected by the timing of the tests and are effective when utilized with automated laboratory equipment. The initial physical change and concentration of the markers caused by the presence of an oxidant-adulterant can remain stable over time. Any change in the concentration of the markers can reinforce or confirm the presence of an oxidant and, thus, adulteration of the urine sample. Advantageously, the marker(s) utilized are naturally present in urine of all primates, including humans.

In one embodiment, uric acid is utilized as a marker in a urine sample. A phosphotungstate reagent can be used to detect the amount of uric acid in the sample. However, phosphotungstate lacks specificity for detection of uric acid. This is believed to be due to the presence of low levels of secondary compounds or constituents, which can be referred to as "non-urate markers" that are found in urine. These non-urate markers include, but are not limited to, ascorbic acid, cystine, cysteine, ergothioneine, and glutathione. These non-urate markers, referred to herein as a Uric Acid Equivalent markers were discovered to also be oxidized when exposed to oxidizing adulterants. An OHist assay of the subject invention advantageously employs, or is at least not inhibited by, this lack of specificity of phosphotungstate and can use the Uric Acid Equivalent beneficially for the indirect detection of oxidizing-adulterants in urine.

Furthermore, the presence of uric acid and other non-urate markers in urine allow phosphotungstate to be used as a chromogen. Specifically, the phosphotungstate reagent of the OHist assay can react with the Uric Acid Equivalents causing urine to turn a blue color, thus enabling quantification of these substances. In the presence of an oxidative-adulterant, the Uric Acid Equivalents can be reduced, lightening the blue color formation and, at certain concentrations, an oxidative-adulterant can eliminate most or all of the blue color. This can result in a reduction in light absorbance at certain wavelengths during colorimetric or spectrophotometric analysis. Advantageously, the embodiments of the subject invention can be used with colorimetric techniques and spectrophotometric devices that can more accurately and easily quantify the amount of Uric Acid Equivalents in the sample of bodily fluid, such as, for example, urine. The addition of oxidative-adulterants, which normally inhibit drug measurement in urine by oxidatively destroying the drugs, can also oxidize uric acid and non-urate markers. The oxidation of these markers can significantly affect their ability to react and form a blue color reaction with the phosphotungstate reagent of the present invention, which is easily detectable by spectrophotometric techniques.

The blue coloration, when analyzed spectroscopically, can indicate the concentration of markers present in the urine sample. In one embodiment, the blue coloration affects light absorbance in the range of from between approximately 580 to approximately 800 nm. In a more particular embodiment, the blue coloration affects light absorbance in the range of from between approximately 600 to approximately 700 nm. In a specific embodiment, the blue coloration affects light absorbance in the range of from between approximately 650 nm to approximately 700 nm.

Figure 3:
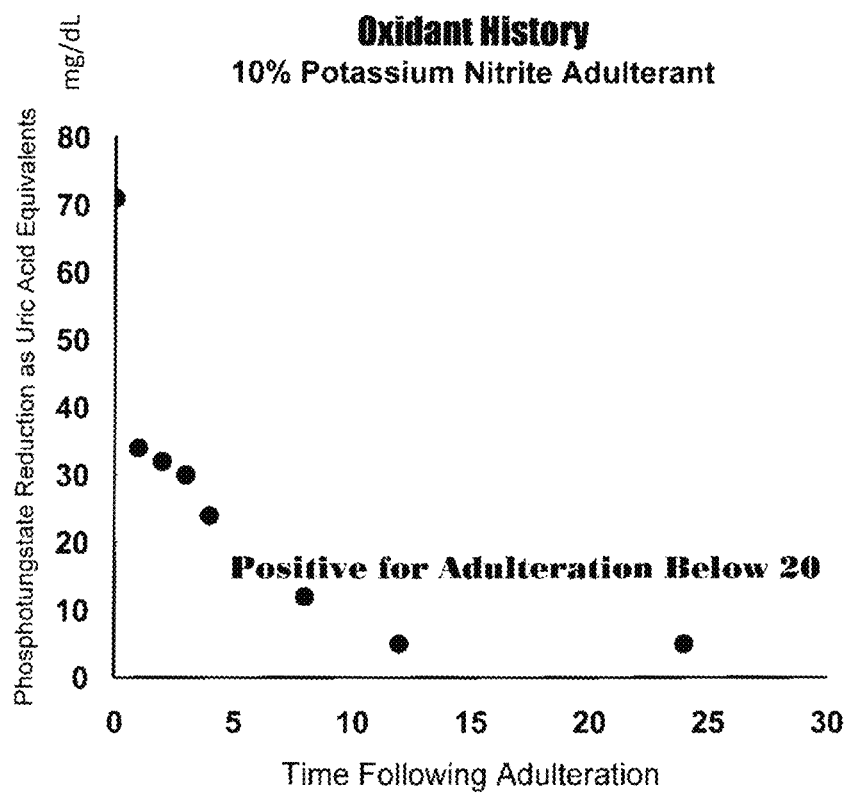
FIG. 3 is a graph of an Oxidant History obtained using the Uric Acid Equivalents in a urine sample that has been adulterated with a solution of 10% potassium nitrate.
Figure 4:
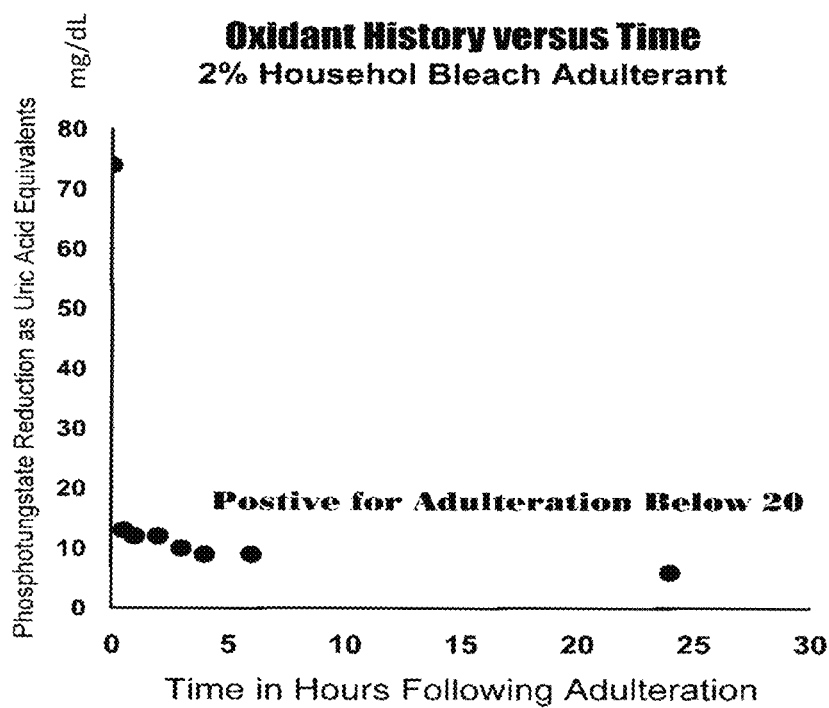
FIG. 4 is a graph of an Oxidant History obtained using the Uric Acid Equivalents in a urine sample that has been adulterated with a solution of 2% bleach.

Ideally, a urine sample with a Uric Acid Equivalent or OHist panel result that the laboratory considers borderline or otherwise suspicious should be retested 24 hours after collection. The oxidant time-history of a sample, as provided by the OHist testing procedures of the subject invention, can provide definitive confirmation of oxidant adulteration of a urine sample. An OHist, as used herein, refers to obtaining historical light absorbance measurements of Uric Acid Equivalents values in a sample over a pre-determined period of time or during a time window. These light absorbance measurements can be used to prepare an OHist for the given time window, which can be a history of the effects of an oxidative-adulterant on a urine sample, if present. As discussed above, the OHist can show how an oxidant adulterant in a urine sample progressively destroys the phosphotungstate-reducing ability of the markers in the urine sample, thereby affecting the light absorbance of the sample at certain wavelengths. Although the initial decrease can be substantial, as indicated by the graphs in FIGS. 2, 3, and 4, the effects can continue, often more slowly, over time.

The level of Uric Acid Equivalents can vary between samples. However, the embodiments of the subject invention can still be effective because the effects of the oxidative-adulterants can continue to reduce the blue color in a sample to levels that are far lower than the lowest end of the range possible. A low cut-off limit can be established to inhibit false positive results, but which can also inhibit false negative results. However, with the embodiments of the subject invention, an oxidative-adulterant that can affect measurements of samples treated with the phosphotungstate reagent of the subject invention can be more easily detected by confirmation testing when conducted at a later time. Absent the presence of an oxidative-adulterant, the levels of uric acid in urine are known to be very stable for a relatively long time period, at least several days. The confirmation test can be carried out by re-assaying and observing changes in the level of reduction capacity of the phosphotungstate reagent, which can only be caused by the presence in the sample of an oxidative-adulterant affecting the markers that make up the Uric Acid Equivalent value. A significant lowering of the phosphotungstate reduction capacity of the urine sample, as indicated by a reduction in the blue coloration of the urine, can thus be a definitive confirmation of the presence of oxidative adulterant, regardless of the original uric acid concentration. Thus, the measurement of phosphotungstate reduction or the levels of the markers, and changes therein, can be useful in both a screening test and a confirmation test.

Certain embodiments of the subject invention utilize a sodium phosphotungstate reagent for reacting with a urine sample. There are several types phosphotungstate that can be utilized with the subject invention. For example, lithium phosphotungstate could also be used in the embodiments of the subject invention. Preferably, the selected phosphotungstate that is utilized is molybdate-free. A person with skill in the art, having benefit of the subject disclosure, would be able to determine any one of several types of phosphotungstate that could be used in the reagent of the subject invention.

In one embodiment of the method of the subject invention, a urine sample is analyzed to obtain a first Uric Acid Equivalents value for the sample utilizing the reagent of the subject invention. However, if the test results show a Uric Acid Equivalents value that is not initially indicative of the presence of an oxidative-adulterant, analysis with the other assays of subject invention may warrant confirmatory testing. In that situation, the sample can be sent to a confirmatory laboratory for further testing. One embodiment of the method of the subject invention includes the confirmatory laboratory conducting further tests of the markers to obtain a second or additional Uric Acid Equivalents values. If the test results of a confirmatory laboratory do not indicate or corroborate adulteration, the one or more Uric Acid Equivalents values can then be compared to the initial Uric Acid Equivalents value obtained by the screening laboratory. All of the Uric Acid Equivalents values, first, second, and any subsequent values, can be plotted to create an OHist. If the OHist confirms that the levels of Uric Acid Equivalents values decreased during the time window of the sample, which is from the time the sample was obtained to the time of the confirmatory testing, then the presence or historical presence of an oxidative-adulterant can be definitively confirmed.

One embodiment of a phosphotungstate reagent can be prepared as follows:

Reagent 1: Phosphotungstate Reagent—1 Liter: Add 27 grams of molybdenum free sodium tungstate to approximately 333 mL deionized water in a reflux vessel. Add 30.9 grams of phosphoric acid. Add boiling chips and reflux gently for 2 hours. Cool to room temperature and then dilute to 1 Liter with deionized water. Add 21.0 grams of Lithium Sulfate and mix.

All ingredients are ACS grade. Molybdinum free Sodium Tungstate was obtained from GFS Chemicals, Powell Ohio 43065. The reagent so prepared is stable for at least 1 year refrigerated at 2-8 degrees Celsius.

When utilized in an automated analyzer of the type used for urine analysis, the following additional buffer reagent and calibrator reagent can be formulated for use in such equipment:

Reagent 2: Carbonate Buffer Reagent—1 Liter. Dissolve 119 grams of ACS grade sodium carbonate to 800 mL of deionized water. Add 7.5 grams sodium hydroxide. Add deionized water to bring the volume to 1 Liter. This reagent is used to buffer the test sample and blank.

The reagent is stable for at least 1 year at ambient temperature 20-30 degrees Celsius.

Reagent 1 and 2 are stable for at least 1 year when packaged together and stored at 2-8 degrees Celsius.

Reagent 3: Uric acid 40 mg/dL Calibrator: 1 Liter—Dissolve 0.63 grams of ACS grade lithium carbonate in 500 mL of Deionized water. Warm to about 45 degrees Celsius. The mixture should not be warmer than 50 degrees Celsius for the next step. Add 400 mg of ACS grade uric acid and mix until dissolved. Dissolve 0.5 grams of sodium azide and then dilute to 1 liter with deionized water. This calibrator is stable for at least 1 year refrigerated at 2-8 degrees Celsius.

One embodiment of the method utilizing the reagents 1, 2, and 3, in automated equipment is as follows:

Manual Preparation of Final Reagent:

Test—Add 100 µL of Urine Sample to 2 mL of Phosphotungstate Test Reagent 1 and mix.

Reagent Blank—Add 100 µL of Deionized water to 2 mL of Phosphotungstate Reagent 1 and mix.

Add 1 mL of Carbonate Buffer Reagent 2 to Reagent Blank and Test Reagent and mix each one separately.

Incubate for 5 minutes at 37 degrees Celsius.

Measure absorbance at 700 nm of Reagent Blank and Test Reagent.

Calibrator absorbance is developed by using the calibrator as a Test.

The Test Net absorbance (Test Absorbance—Blank Absorbance) is used to calculate the Uric Acid Equivalent result as follows:

(Test Net Absorbance/Calibrator Net Absorbance)× Calibrator Absorbance=Value of Calibrator The absorbance measurement may be made at 600-700 nm. No secondary bichromatic wavelength should be used.

Following are specifications for testing a urine sample with a Mindray BS-200 automated chemical analyzer. These settings are intended as guidelines and those with skill in the art would recognize that the parameters can vary between instruments.

| Test: | OX Hist |
|---|---|
| No. | User Defined |
| Full Name: | Oxidant History |
| Reaction Type: | Endpoint |
| Pri. Wave | 670 nm |
| Sec Wave | none |
| Direction: | Increase |
| Reac. Time: | 0 and 11 |
| Incubation Time: | 3 |
| Unit: | Mg/dL UAEq |
| Precision: | Integer |
| R1: | 180 |
| R2: | 90 |
| Sample Volume; | 10 |
| Mixed Reagent Blank | Optional |
| Compensate: Slope:1 | Intercept: 0 |

Following are specifications for testing a urine sample with the Beckman-Coulter AU 400, AU 400e, AU 480, AU 640, AU640e and AU680 Series automated chemical analyzers. These settings are intended as guidelines and those with skill in the art would recognize that the parameters can vary between instruments.

| Reagent ID: | User defined | | |
|---|---|---|---|
| Test Name: | Oxidant History | | |
| Sample Volume: | 10 | | |
| R1 Volume: | 100 | | |
| R2 Volume: | 50 | | |
| Wavelength: Pri: | 700 | Sec. | None |
| Method: | + | | |
| Reaction Slope: | POS | | |
| Measuring Point 1: First | 25 | Last | 27 |
| Measuring Point 1: | (Not Applicable) | | |
| Calibration Type: | AA | Formula: | Y = AX + B |

The reagents and methods described above can be used to exploit the kinetics of Uric Acid Equivalents measurement by performing a screening assay on a urine sample soon after collection and then repeating the screening assay hours or even days following the first test. For example, the collecting site or first immunoassay screening laboratory can test the sample and obtain an initial Uric Acid Equivalents value for the sample. If the initial value concludes the possible presence of an adulterant, the results can be reported to the confirmatory laboratory. The confirmatory laboratory can also obtain one or more Uric Acid Equivalent values on the same sample at a later time. The results of the initial Uric Acid Equivalents value can be compared with the results of the one or more Uric Acid Equivalents values obtained later by the confirmatory laboratory and plotted to obtain an OHist. If analysis of the OHist shows a reduction in the Uric Acid Equivalents values over time, the presence of an oxidative-adulterant can be considered definitive proof of the use of an oxidative-adulterant in the sample. Even if the analysis of the Uric Acid Equivalents values do not fall below the mandated cutoff level indicative for positive adulteration, adulteration can still be definitively proven if the Uric Acid Equivalents values obtained from confirma tory laboratory tests have fallen significantly during the time window of the sample.

II. Two Assays for Detecting Counterfeit Urine Utilizing Short-Duration (SD) Acid Phosphatase (AP) and Long-Duration (LD) Alkaline-Phosphatase (ALP) Markers in Urine Embodiments of a Counterfeit Urine assay of the subject invention are unique in their ability to detect the absence of a constituent in the urine sample, rather than the presence of a constituent, as an indication that the sample is not true human urine. U.S. patent application Ser. No. 15/961,003, filed on Apr. 24, 2018, discloses assays and methods of use that can be utilized with embodiments of the subject invention to detect counterfeit urine. The entirety of U.S. Ser. No. 15/961,003 is hereby incorporated by reference.

Embodiments of the SD and LD counterfeit urine assays of the subject invention employ two different markers normally found in urine. Advantageously, the markers utilized with the testing methodology of the subject invention are activated under significantly different conditions and detectable under similar conditions. A further advantage of these markers is their labile nature that makes them impractical to use as additives in counterfeit urine products. Furthermore, while efforts can be made to mimic the presence of these markers, such as by addition of indicator dyes, the embodiments of the subject invention can detect such efforts.

Specifically, embodiments of the subject invention utilize the labile markers acid phosphatase (AP) and alkaline phosphatase (ALP) to detect whether urine is "true urine," being of human origin, or is a counterfeit urine product. AP and ALP are preferred enzyme markers because they are present in urine produced by both males and females and have poor in vitro stability. These markers are temperature sensitive, which makes them unstable after sample collection. For example, AP is a short-duration (SD) marker, often degrading in a sample within 3 days. In contrast, ALP is a long-duration (LD) marker, often degrading in about a week to 10 days. Samples are usually tested within a few days after collection. If AP in the sample has degraded before testing, it is still likely at least some ALP will remain in the sample and can provide results.

In a further embodiment, the subject invention utilizes the chromogenic substrates thymolphthaleine monophosphate and p-nitrophenyl phosphate, which are catalyzed by AP (at pH 4-6) and ALP (at pH 8-10), respectively. Thymolphthalein monophosphate and p-nitrophenyl phosphate are advantageous because they are catalyzed at significantly different pH levels, but produce chromogens that are activated under identical alkaline conditions. The subject invention utilizes these advantageous characteristics to create a single test control for detecting the presence of both of these chromogens.

Advantageously, these markers have a labile nature that makes them unsuitable, or at least impractical, as additives to counterfeit urine products. The constituents are temperature sensitive causing them to degrade within a few days and become undetectable, often before the counterfeit urine product can be used. The reagents according to the subject invention are safe and non-toxic.

The substrate thymolphthalein monophosphate is shown below:

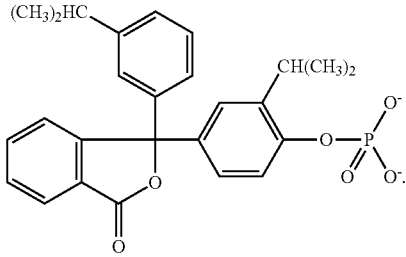

Thymolphthalein monophosphate is catalyzed by AP at between approximately pH 4 to approximately pH 6. When combined with an aliquot of a sample of urine, AP in the urine hydrolyzes this substrate thereby producing free thymolphthalein. Thymolphthalein is a colorless product at the acid pH necessary for hydrolysis. When exposed or subjected to alkaline conditions, thymolphthalein exhibits a blue color. Thymolphthalein monophosphate is catalyzed to form thymolphthalein as follows (Equation I):

Equation I

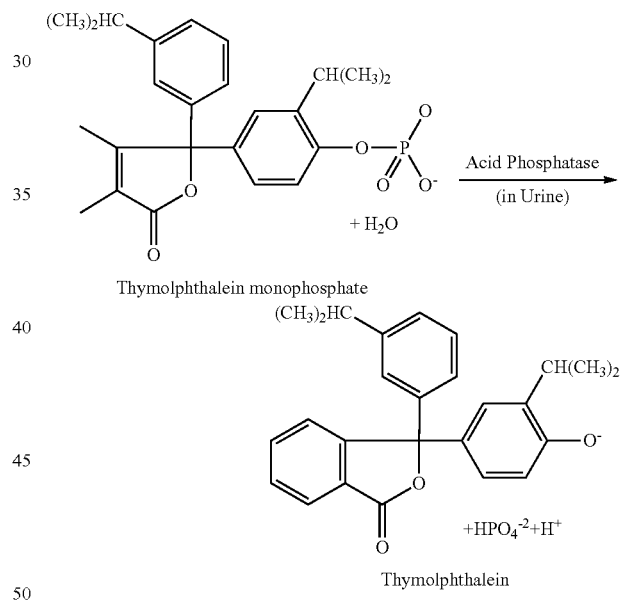

Another substrate utilized with embodiments of the subject invention is p-nitrophenylphosphate (shown in the acid form):

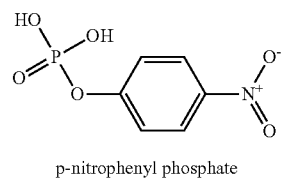 [SMILES: O=[N+]([O-])c1ccc(OP(=O)(O)O)cc1]

p-nitrophenyl phosphate

P-nitrophenyl phosphate is catalyzed by urinary alkaline phosphatase (ALP) at between approximately pH 8 and approximately pH 11. P-nitrophenyl phosphate is also catalyzed by urinary acid phosphatase at between approximately pH 5 and approximately pH 6. When added to a sample of urine, alkaline phosphatase (ALP) in the urine hydrolyzes the p-nitrophenyl phosphate substrate, thereby producing free p-nitrophenol. The p-nitrophenol turns yellow at the pH necessary for hydrolysis, thus is self-indicating. Acid phosphatase (AP) also catalyzes the hydrolysis of p-nitrophenol phosphate to liberate p-nitrophenol, which under the acid is colorless at the acid pH required for this AP reaction. Thus, a second step that alkalinizes the solution is necessary to activate p-nitrophenol as a chromagen that indicates the hydrolysis of p-nitrophenyl phosphate.

p-nitrophenylphosphate is catalyzed by ALP as follows (Equation II):

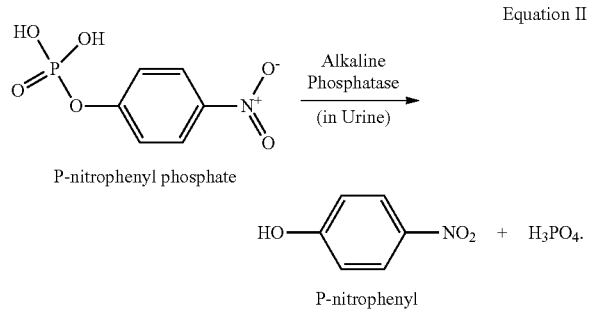

Equation II

P-nitrophenyl phosphate

P-nitrophenyl

Thus, both thymolphthalein and p-nitrophenol are chromogens that are color-activated under alkaline conditions, such that thymolphthalein turns blue and p-nitrophenyl turns yellow.

Automated analyzers typically utilize liquid reagents. In one embodiment, the reagents of the subject invention are formulated as liquids for use in an automated analyzer. When a sample treated according to the subject invention is analyzed spectrophotometrically, the blue color produced by thymolphthalein is absorbed at a wavelength of approximately 600 nm. The yellow color produced by p-nitrophenol is absorbed at a wavelength of between approximately 405 nm and approximately 410 nm.

Figure 5:
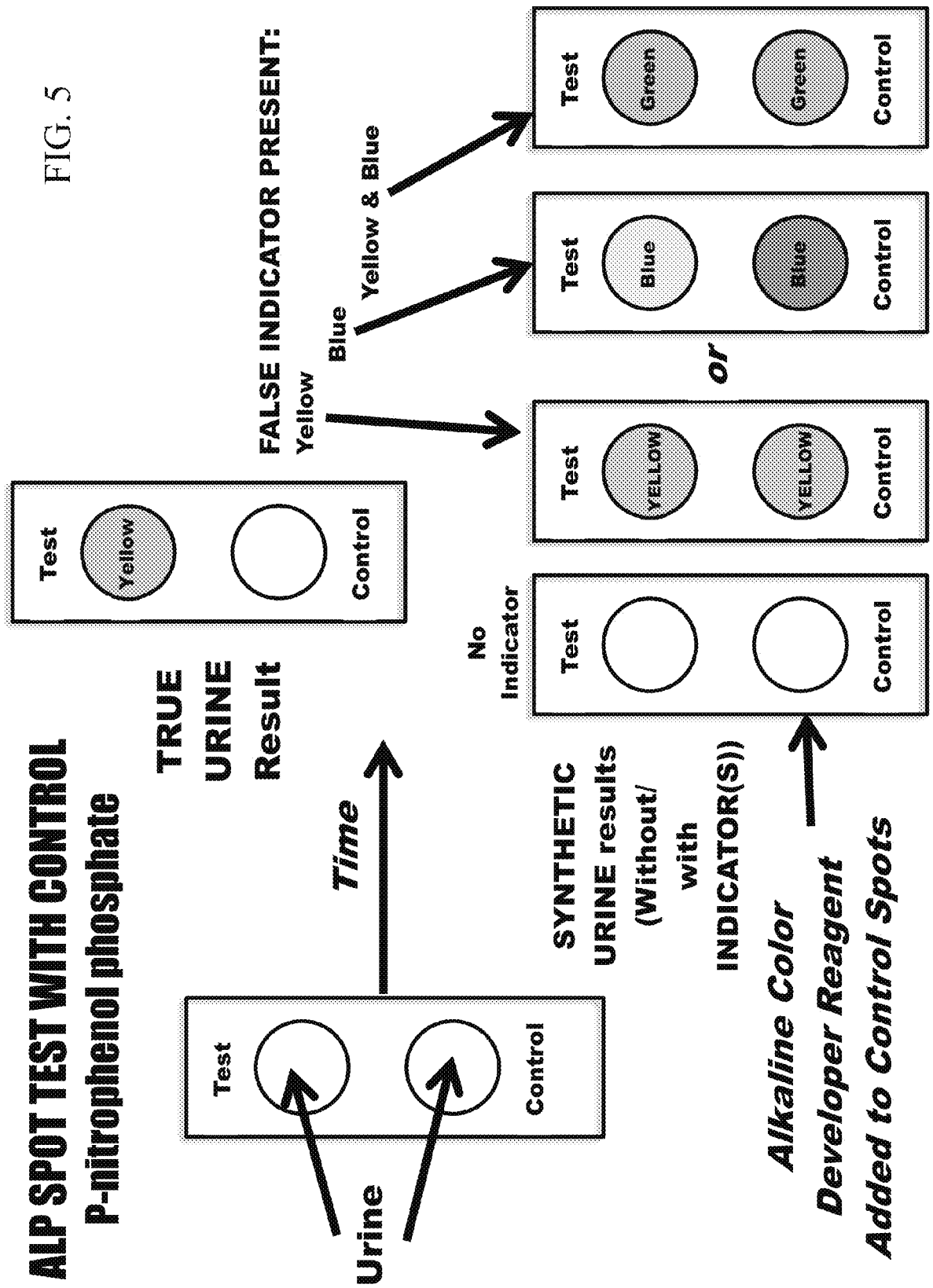
FIG. 5 illustrates a method for detecting the presence of alkaline phosphatase (ALP), a long-duration (LD) bio-marker in a urine sample, according to embodiments of the subject invention. The method is illustrated utilizing a dip stick with a Test spot comprising p-nitrophenyl phosphate substrate to which a sample can be added and that, according to embodiments of the subject invention, reacts with alkaline phosphatase (ALP) in true urine to form the chromogen p-nitrophenol. The control has neither the substrate nor the chromogen. The p-nitrophenol turns yellow at the alkaline pH necessary for the ALP, if present in the sample, to catalyze the p-nitrophenyl phosphate substrate. When an alkaline pH reagent is added to the Control spot, the sample can be counterfeit urine if it also turns dark yellow indicating that p-nitrophenol was present in the sample and was not formed as a result of alkaline phosphatase in the urine. It can also be seen in this Figure that if the thymolphthalein chromogen was added to the sample, the Test spot, as well as the Control spot turn blue, due to the alkalinity of both spots. Further, if both chromogens were added to the sample, the Test spot and the Control spot turn green, a result of the combination of both chromogen colors.
Figure 6:
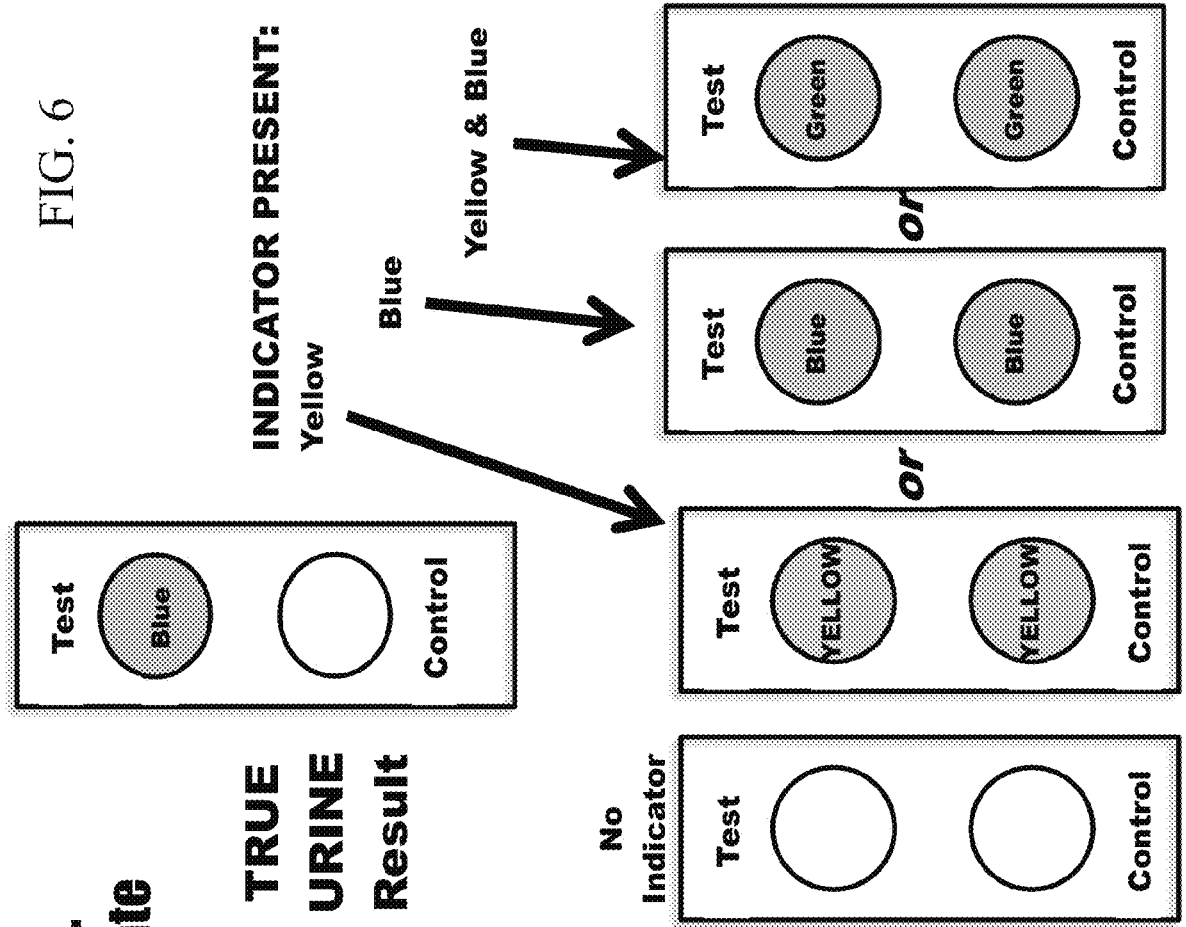
FIG. 6 illustrates a method for detecting the presence of acid phosphatase (AP), a short-duration (SD) bio-marker in a urine sample, according to embodiments of the subject invention. The method is illustrated utilizing a dip stick with a Test spot comprising a thymolphthalein monophosphate substrate to which the sample can be added and that, according to embodiments of the subject invention, react with acid phosphatase (AP) present in true urine to form the chromogen thymolphthalein. Thymolphthalein is colorless at the acid pH necessary for the AP, if present in the sample, to catalyze the thymolphthalein monophosphate substrate. The Control spot has neither the substrate, nor the chromogen. When an alkaline pH reagent is added to the Test spot and the Control spot, the chromogen formed at the Test spot is activated and imparts a blue color to the Test spot. The Control spot can indicate whether the sample is counterfeit urine if it also turns blue, indicating that thymolphthalein was present in the sample and was not formed as a result of acid phosphatase in the urine. It can also be seen in this Figure that if the p-nitrophenol chromogen was added to the sample, the Test spot, as well as the Control spot turn yellow. Further, if both chromogens were added to the sample, the Test spot and the Control spot turn green, a combination of both chromogen colors.
Figure 7:
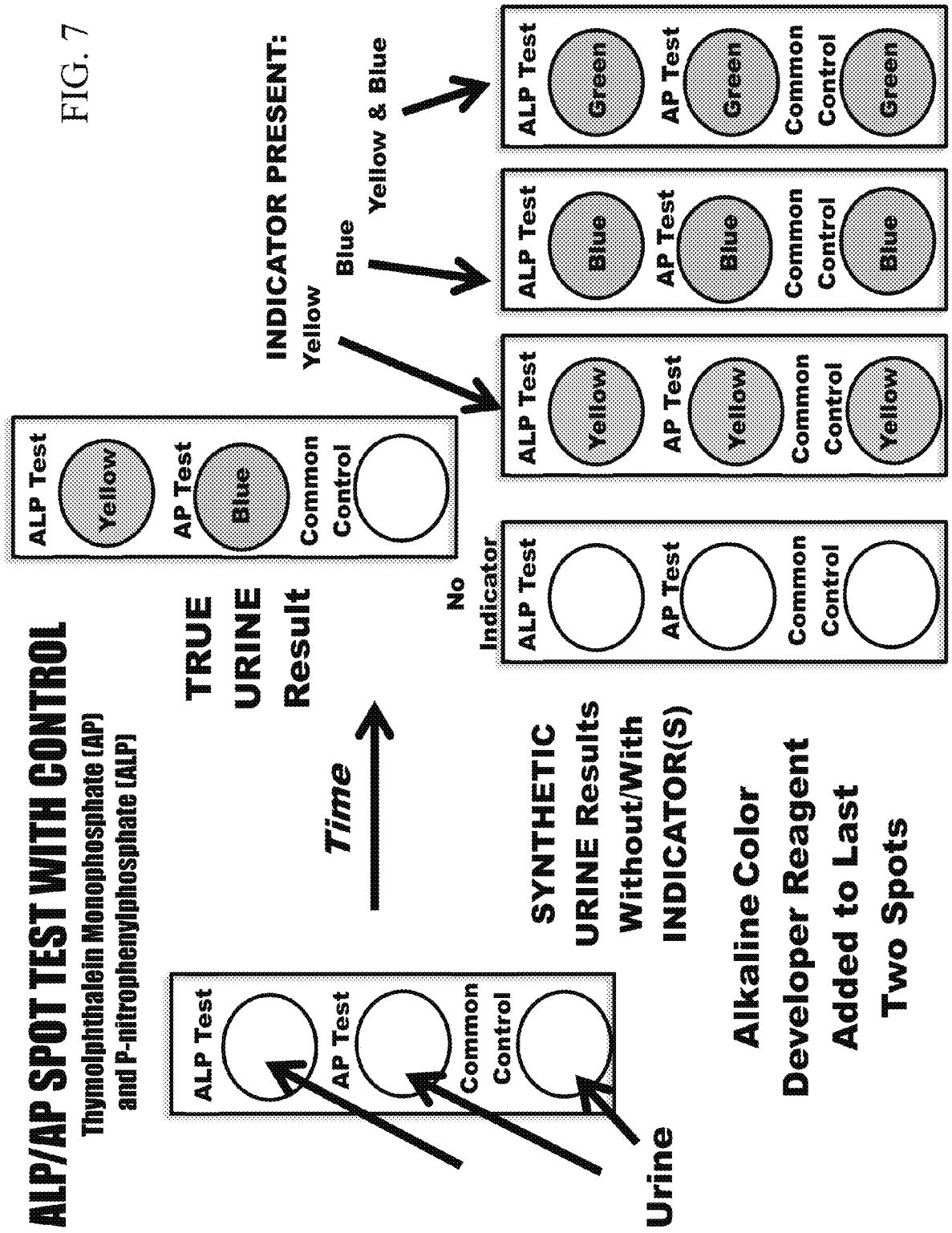
FIG. 7 illustrates a method for detecting the presence of both acid phosphatase (AP) and alkaline phosphatase (ALP) in a sample, according to embodiments of the subject invention. The method is illustrated utilizing a dip stick with one spot comprising p-nitrophenyl phosphate substrate (labeled as ALP) and another spot comprising thymolphthalein monophosphate substrate (labeled as AP), as well as a third Control spot containing neither of the substrates, nor their chromogens. According to embodiments of the subject invention, when true urine is added to the Test spots, the substrates react with either the alkaline phosphatase (ALP) or acid phosphatase (AP) to form the respective chromogens p-nitrophenol and thymolphthalein. If the sample is true urine, the ALP Test spot turns yellow and the AP Test spot and Control spot remain colorless. When an alkaline pH reagent is added to the AP Test spot and the Control spot, the AP Test spot turns blue and the Control spot remains uncolored. The Control spot indicates a counterfeit, thus invalid, sample if it turns either blue or yellow, indicating that the chromogen was likely added to the sample and was not formed as a result of alkaline or acid phosphatase in the urine. If the control turns green, it indicates that both chromogens were added to the sample and were not formed as a result of alkaline or acid phosphatase in the urine, thus, an invalid sample. It can also be seen that if either chromogen was added to the sample, all of the Test spots, as well as the Control spot turn yellow and/or blue. Further, if both chromogens were added to the sample, all of the Test spots and the Control spot turn green, a combination of both chromogen colors.

The stability of the thymolphthalein monophosphate and p-nitrophenyl phosphate substrates makes them useful for dip stick or spot tests. Spot tests are well-known in the art and can have a liquid, semi-solid, or solid transport medium. For the sake of providing a visual representation of the embodiments of the subject invention, reference will be made to a dipstick methodology, as shown in FIGS. 5, 6, and 7. The ability to formulate the substrates of the subject invention for dipstick spot tests is known in the art and will not be described in detail here.

Embodiments of the subject invention utilize reagent systems, which include substrate reagents that are catalyzed by either ALP and/or AP and a color-developer reagent that activates or enhances the appearance and color of the resulting chromogen. The reagent system embodiments can also utilize a control reagent, which advantageously confirms the presence or absence of one or both of the chromogens.

One embodiment of a reagent system includes a substrate reagent comprising the substrate p-nitrophenyl phosphate that is buffered to between approximately pH 9.5 to approximately pH 11, which promotes formation of the chromogen in the presence of the catalyst. In a further embodiment, the reagent system includes a control reagent, which comprises no p-nitrophenol or p-nitrophenyl phosphate. The control reagent can also comprise all or most of the constituents of the substrate reagent, except for the substrate and the chromogen. In a yet further embodiment, the p-nitrophenyl phosphate reagent system has an alkaline color-developer reagent buffered to between approximately pH 9.5 to approximately pH 11. The color-developer reagent can be utilized with the control to determine whether a sample is true urine or a counterfeit urine product.

It can be seen in FIG. 5 an example wherein the p-nitrophenol phosphate reagent system is illustrated with a dip stick method. In the dip stick example shown in FIG. 5, the upper Test spot comprises the substrate reagent and the lower Control spot comprises the control reagent, which are, initially, colorless. When the spots are saturated with a sample, several reactions can occur, depending upon the constitution of the sample. True urine causes the upper Test spot to turn a distinctive yellow color, by the reaction of the ALP in the urine with the p-nitrophenyl phosphate, which cleaves the phosphate moiety, leaving the chromogen p-nitrophenol. When saturated with true urine, the Control spot remains colorless or can appear to turn the same color of the sample. The Control spot, at this point, does not have the same yellow color as the Test spot. The addition of other ingredients to a sample can cause the same result as true urine, i.e., turn the Test spot yellow. Advantageously, the color-developer reagent of the subject invention can detect these other potential additives, if present.

With regard to FIG. 5, to confirm whether the constitution of the sample is true urine or a counterfeit urine product, the Control spot is treated with the color-developer reagent of the p-nitrophenyl phosphate reagent system, which changes the Control spot to an alkaline pH. If, after addition of the color-developer reagent, the Control spot turns the same or a similar yellow color as the Test spot, it indicates that the p-nitrophenol chromogen was likely added to the sample, which further indicates the sample being a counterfeit urine product or was at least subject to other tampering and, thus, invalid.

A further advantage of this embodiment of the p-nitrophenyl phosphate reagent system, is that it is also possible to detect the presence of thymolphthalein that may have been added to the sample. If the Test spot and/or the Control spot turn blue, as shown in FIG. 5, it indicates that thymolphthalein was added to the sample, which reacts, at least mildly, in the alkaline pH of the Test spot, such that both spots are imbued with a blue color, thus, indicating invalidity of the sample. Addition of the second, alkaline color-developer reagent to the Control spot can turn it blue, providing further indication that thymolphthalein was likely added to the sample, as indicated in FIG. 5, thus, another indication of invalidity of the sample. If the Test spot and/or the Control spot turns green, both p-nitrophenol and thymolphthalein were added to the sample, whereby the color transformations of the yellow and blue chromogens combine to forms the green color, as also shown in FIG. 5, again, indicating that the sample is invalid.

One embodiment of a Reagent System for detection of p-nitrophenol using automated equipment is described below:

Substrate Reagent: Alkaline Buffered and a Combination of the Following Component A and Component B.

| Component A: | 31 grams | 2-amino-2-methyl-1-propanol (AMP) |
|---|---|---|
| | 0.2 grams | Proclin 300 |
| | 0.6 grams | N-hydroxyethylene-diaminetriacetic acid (HEDTA) |

Combine the above ingredients with approximately 800 ml deionized water and mix to dissolve to form solution #1.

| | 0.3 grams | Zinc Sulfate•7H$_2$O |
|---|---|---|

Add to solution #1 and mix to dissolve to form solution #2.

| | 0.4 grams | Magnesium Acetate•4H$_2$O |
|---|---|---|

Add to solution #2 and mix to dissolve to form solution #3.
Adjust pH of solution #3 to 10.2 +/− 0.05 using 6 N HCl, to form solution #4.

| | 4 grams | Brij 35 30% solution |
|---|---|---|

Add to solution #4 and mix to dissolve to form solution #5. Reagent #1 is formed by adding deionized water to solution #5 to make 1 Liter and mix to dissolve. Avoid excess exposure to air following pH adjustment. Note: This is a buffered solution.

| Component B: | 900 mL | Deionized water |
|---|---|---|
| | 0.5 grams | Proclin 300 |
| | 2.0 grams | Imidazol |
| | 20 grams | p-nitrophenol phosphate disodium salt (hydrate form) CAS No. 123359-43-3 |

Adjust to pH 6.5+/−0.01 with pure 6 N HCl and bring volume to 1000 ml with deionized water.

Control Reagent: Component B is replaced with deionized water and an alkaline solution, such as Component A mentioned above, is added as in the test. This type control is only required for dip-stick tests or where the reagent is measured as an end-point assay. If the p-nitrophenol phosphate reagent is detected by an automated device as a fixed time or kinetic assay, the initial absorbance of the reagent may be observed as a control and limits set for the initial absorbance if permitted by the automated device. Otherwise, a control as provided above must be performed to detect addition of adulterants to the counterfeit urine.

| Calibrator: | 100 Units/L | Urinary tract Protein-LD |
|---|---|---|
| | 1.0 Liter | 50% Glycerol in Deionized water |
| | 1.6 grams | Tris Hydrochloride |
| | 0.3 grams | Magnesium Chloride |
| | 0.02 grams | Zinc Chloride |

To the above solution add 50 Units of Alkaline phosphatase CAS RN 9001-78-9.

| Stock Calibrator: | 140 mg | p-nitrophenol |
|---|---|---|
| | 0.2 g | Proclin 300 |
| | 300 mg | Imidazol |

Combine with approximately 800 mL of deionized water and mix to dissolve. Adjust pH to 6.5 using diluted HCl. Final Calibrator is Stock Calibrator diluted 1:250 with deionized water to obtain a Final Calibrator solution having the equivalent of 100 Enzyme Units (Urinary Tract Protein). Note: An enzyme unit (U) is specific to particular enzyme and is defined as the amount of the enzyme that catalyzes the conversion of 1 micro mole of substrate per minute.

Following are specifications for testing a urine sample with a Mindray BS-200 automated chemical analyzer. These settings are intended as guidelines and those with skill in the art would recognize that the parameters can vary between instruments.

| Test: | UALP |
|---|---|
| No. | User Defined |
| Full Name: | Alkaline Phosphatase |
| Reaction Type: | Fixed-time |
| Pri. Wave | 510 nm |
| Sec Wave | 630 |
| Direction: | Increase |
| Reac. Time: | 0 and 2 |
| Incubation Time: | 20 |
| Unit: | UALP Units |
| Precision: | Integer |
| R1: | 180 |
| Sample Volume; | 46 |
| Mixed Reagent Blank: | |
| Compensate: | Slope: 1 Intercept: 0 |

Note: The control procedure for the above is the same as the test procedure, but uses the control reagents. The calibration for the above is the same as the test procedure.

Following are specifications for testing a urine sample with the Beckman Coulter AU 400, AU 400e, AU 480, AU 640, AU640e and AU680 Series automated chemical analyzers. These settings are intended as guidelines and those with skill in the art would recognize that the parameters can vary between instruments.

| Reagent ID: | User defined | |
|---|---|---|
| Test Name: | True Urine LD | |
| Sample Volume: | 35 | |
| R1 Volume: | 120 | |
| R2 Volume: | 30 | |
| Wavelength: Pri: | 405 Sec. | — |
| Method: | FIXED TIME | |
| Reaction Slope: | POS | |
| Measuring Point 1: | First 13 | Last 27 |
| Units: | UTP Units | |
| Calibration Type: | AA Formula: | Y = AX + B |
| Point 1 | CONC: 0 | |
| Point 2 | CONC: 100 | |

Note: The control procedure for the above is the same as the Test procedure, but uses Control Reagent #1.

In another embodiment, a substrate reagent comprises thymolphthalein monophosphate and is buffered to between approximately pH 4 and approximately pH 6. This reagent reacts with AP to promote the formation of the chromogen thymolphthalein. At this pH, there will typically be no formation of the color of the chromogen. In a further embodiment, the thymolphthalein monophosphate reagent system has a color-developer reagent having an alkaline pH of between approximately 9.5 to approximately 11. This can be similar to the color developer reagent utilized with the p-nitrophenyl phosphate substrate reagent, described above. In one embodiment, the control reagent utilized with this embodiment of the reagent system can comprise all or most of the constituents of the substrate reagent, but no thymolphthalein monophosphate substrate, nor any thymolphthalein, which is the chromogen formed from p-nitrophenyl phosphate when catalyzed with AP.

FIG. 6 illustrates a non-limiting example of a dip stick on which the substrate reagent and the control reagent have been stabilized onto specific test spots on the dipstick. In one embodiment, the first substrate reagent is stabilized in a fashion that will provide the necessary acidic pH for the substrate to be catalyzed upon addition of true urine. It will be understood by a person skilled in the art that this reagent system can be in liquid form and the method can be utilized with automated chemical analyzers. With regard to FIG. 6, which shows a non-limiting example of a dip stick method, the upper Test spot comprises the substrate reagent and the lower Control spot comprises the control reagent, which are both initially colorless. When the spots are saturated with a sample, several reactions can occur depending upon the nature of the sample. True urine causes the Test spot to turn a blue color, due to reaction of the AP in the urine with the p-nitrophenyl phosphate, which cleaves the phosphate moiety, leaving the chromogen p-nitrophenol. When saturated with true urine, the Control spot remains colorless or appears as the same color as the sample, e.g., pale yellow, but does not have the same blue color as the Test spot. However, the addition of other ingredients to a sample can cause the same results as true urine. Advantageously, the color-developer reagent of the subject invention can detect whether these other ingredients have been added to the sample.

With regard to FIG. 6, when the Test spot and Control spot are treated with the color-developer reagent of the reagent system, the Test spot and Control spot are changed to an alkaline pH, thereby activating the color change of the thymolphthalein to blue. If, after addition of the color-developer reagent, the Test spot turns blue and the Control spot remains colorless, it indicates that the sample was true urine, valid, and thymolphthalein liberated from the thymolphthalein monophosphate substrate was present on the Test spot. If, after addition of the color-developer reagent, neither the Test spot, nor and the Control spot turn blue, it indicates that the sample did not contain AP to react with the thymolphthalein monophosphate substrate and was invalid. This can indicate that the sample was a counterfeit urine product or was otherwise subject to tampering. Counterfeit urine products or other tampering of the sample can also be suspected if, after addition of the color-developer reagent, the Control spot turns the same or a similar blue color as the Test spot, an indication that the thymolphthalein chromogen was added to the sample.

Furthermore, with this embodiment of the reagent system, it is possible to detect the presence of p-nitropheneol that may have been added to the sample. If, after addition of the color-developer reagent the Test spot and/or the Control spot turn yellow, as shown in FIG. 6, it can be an indication that p-nitrophenol was likely added to the sample. If the Test spot and/or the Control spot turns green, it can be an indication that both p-nitrophenol and thymolphthalein were likely added to the sample, whereby the color transformations of the yellow and blue chromogens combine to form the green color, as also shown in FIG. 6. FIG. 7 illustrates a comparison of the AP and ALP assays by demonstrating the color effects on a dipstick embodiment that includes both assays.

One embodiment of a Reagent System for detection of thymolphthalein using automated equipment is described below:

Substrate Reagent: comprises Component A and Component B, which are added in a 50/50 ratio to obtain the final concentration:

| Component A: | 17.68 grams | Sodium Acetate, added to approximately 400 mL deionized water and mix until dissolved |
| --- | --- | --- |
| | 1.6 grams | Citric Acid followed with sufficient Acetic Acid (redistilled) to adjust pH to 6.0 @ 25° C. |
| | 0.2 grams | Proclin 300 |
| | | Add deionized water to obtain final volume of 500 mL |
| Component B: | 5.0 grams | Brij 35 detergent, added to 500 mL deionized water and mix until dissolved |
| | 1.0 grams | Thymolphthalein monophosphate sodium salt and mix until dissolved |

Combine equal parts of Component A and Component B to obtain a final solution of Substrate Reagent. For example, 500 mL of Component A can be combined with 500 mL of Component B to obtain 1 liter of Substrate Reagent. The Substrate Reagent should be stored refrigerated at between 4°-8° C., away from light.

| Color-Developer reagent: | 20 grams | Sodium Hydroxide |
| --- | --- | --- |
| | 53 grams | Sodium Carbonate (Anhydrous) |

Combine with 1 liter of deionized water to obtain final concentration and volume.

Control Reagent: 500 mL of deionized water and 500 mL of Component A added.

| Calibrator: | 100 | Units | Urinary Tract Protein |
| --- | --- | --- | --- |
| | 700 | mL | n-propanol |
| | 300 | mL | Deionized water |
| | 20 | mg | Thymolphthalein |

The Urinary Tract Protein Units are arbitrary and based upon the amount of thymolphthalein produced during the time of incubation of Component A with a given ratio of component A to urine. Thus, if the time of incubation is doubled, the value of the calibrator can be cut in half. If the urine volume to Component A is lowered by decreasing sample volume, the value can be increased proportionately. The arbitrary units are intended to avoid traditional enzyme measurement and the marker(s) are to be described as Urinary Tract Glyco-proteins, so as to obscure the identity of subversion additions to the counterfeit urine.

Following are specifications for testing a urine sample with a Mindray BS-200 automated chemical analyzer. These settings are intended as guidelines and those with skill in the art would recognize that the parameters can vary between instruments.

| | |
|---|---|
| Test: | True Urine SD |
| No. | User Defined |
| Full Name: | True Urine |
| Reaction Type: | Fixed-time |
| Pri. Wave | 578 nm |
| Sec Wave | 670 |
| Direction: | Increase |
| Reac. Time: | 0 and 2 |
| Incubation Time: | 20 |
| Unit: | UTP Units |
| Precision: | Integer |
| R1: | 180 |
| R2: | 40 |
| Sample Volume: | 46 |
| Mixed Reagent Blank: | |
| Compensate: | Slope 1 Intercept: 0 |

Following are specifications for testing a urine sample with the Beckman Coulter AU 400, AU 400e, AU 480, AU 640, AU640e and AU680 Series automated chemical analyzers. These settings are intended as guidelines and those with skill in the art would recognize that the parameters can vary between instruments.

| | | |
|---|---|---|
| Reagent ID: | User defined | |
| Test Name: | True Urine | |
| Sample Volume: | 30 | |
| R1 Volume: | 123 | |
| R2 Volume: | 43 | |
| Wavelength: Pri: | 600 Sec. | 700 |
| Method: | FIXED TIME | |
| Reaction Slope: | POS | |
| Measuring Point 1: | First 14 | Last 16 |
| Measuring Point 1: | (Not Applicable) | |
| Calibration Type: | 2AB | Formula: Polygonal |
| Point 1 H20 | CONC: 0 | |
| Point 2 Cal | CONC: 100 | |

Note: the control procedure is the same as the Test procedure.

III. Specific Gravity Assay Utilizing Sodium (Na+) and Potassium (K+) Markers in Urine The subject invention provides methods and reagents useful for analysis and measurement of specific constituents in a urine sample that can be used to derive a Specific Gravity Index (SGI) for a urine sample. When the SGI of a given urine sample is compared to the SGI of known normal urine samples, results can be used to determine whether the given sample was adulterated. U.S. patent application Ser. No. 15/651,334, filed Jul. 17, 2017, discloses assays and methods of use that can be utilized with embodiments of the subject invention to detect adulteration of a urine sample. The entirety of U.S. Ser. No. 15/651,334 is hereby incorporated by reference.

Specific gravity of a liquid is a measure of the weight of a liquid divided by the weight of water of equal volume. The constituents found in the highest concentrations in urine are sodium chloride and potassium chloride and, as such, contribute most to the specific gravity measurement for a urine sample. However, there are other constituents, such as urea, which also contribute to the overall specific gravity of a urine sample. A Specific Gravity Index, (SGI), according to the subject invention, is a measurement obtained by utilizing a subset of the constituents found in a urine sample. More specifically, the SGI is a measurement of the weight of the non-aqueous subset of constituents of the sample per unit volume. Advantageously, the subset of constituents can also be used as markers, according to the subject invention, for automating analysis of a urine sample, so as to obtain a SGI.

Figures 8, 9:
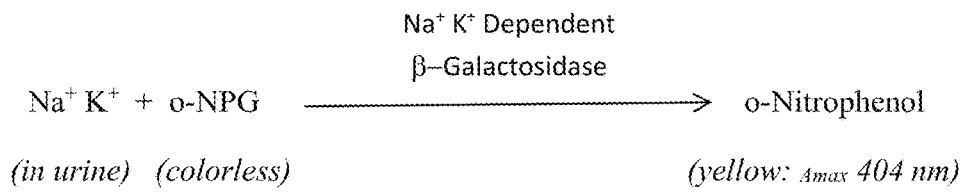
FIG. 8 is an equation showing one embodiment of the reaction method of the subject invention.
FIG. 9 is a table showing the results of the Specific Gravity Index (SGI) measurements on normal urine samples and samples adulterated with common adulterants. Typically, the effects of an adulterant are not measurable below 10% w/v. It can be seen that, with embodiments of the subject invention, adulterant concentrations in a sample of 1% and 5% w/v can be detected and indicate the sample is positive for adulteration. This indicates a high sensitivity for this test.

One embodiment of the subject invention utilizes the sodium (Na+) and potassium (K+), naturally found in a urine sample, as markers. In a further embodiment, these same markers are used to obtain a SGI for the sample. In a specific embodiment, a sodium-potassium dependent β-Galactosidase is utilized along with an indicator chromogen of o-nitrophenylgalactoside (o-NPG). In one embodiment, the method of the subject invention results in the formation of a yellow color due to cleavage of the o-NPG into o-nitrophenol, a molecule that can be analyzed by the spectrophotometry methods utilized in most clinical analyzers to obtain a SGI for the given sample. The chromogen can be cleaved to o-nitrophenol by using the sodium or potassium activated β-Galactosidase. Thus, the amount of sodium and/or potassium in a given urine sample can dictate the amount of cleaved o-NPG created by the reaction. A measurement of both sodium and potassium, can be extrapolated to yield a total mEq/L of both substances in the sample In a specific embodiment, the reagent and method of the present invention employ sodium-potassium dependent beta-galactosidase (β-galactosidase) in conjunction with an indicator chromogen of o-nitrophenylgalactoside (o-NPG). The reaction causes the chromogen to be cleaved into o-nitrophenol by the sodium and/or potassium activated β-galactosidase. Advantageously, the rate at which the yellow o-nitrophenol is produced from the colorless o-NPG can be measured spectrophotometrically at a primary wavelength of 405-410 nm. FIG. 8 illustrates this reaction. The rate of increase in absorbance at 405 nm-410 nm is proportional to total sodium and potassium concentration in the sample. Colorimetric measurements outside a known normal range for a SGI of urine can be an indication of abnormal levels of sodium and/or potassium in the sample. This can be an indication that the sample integrity has been compromised and the sample is not valid.

Figure 10:
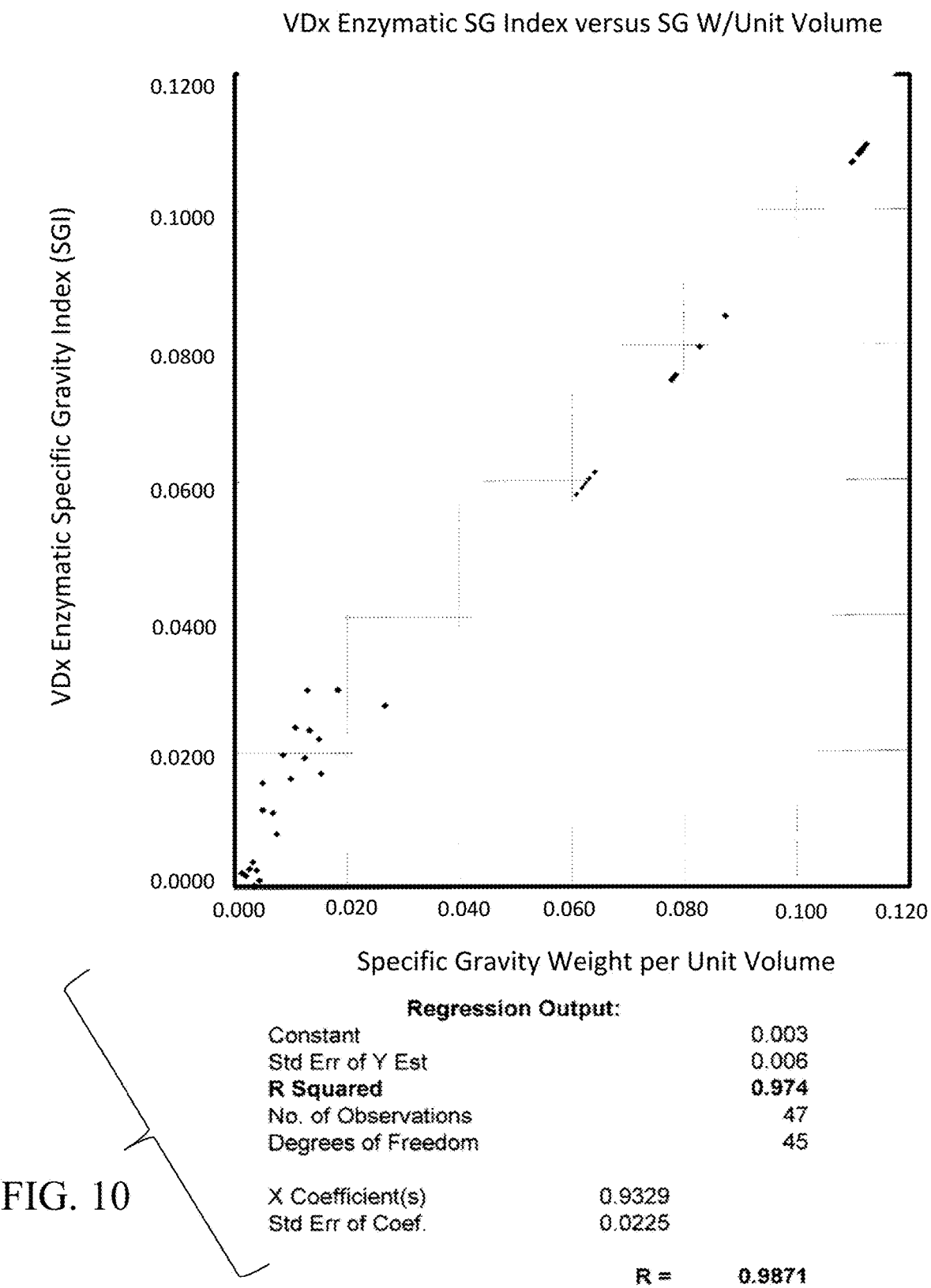
FIG. 10 is a graph comparing the actual specific gravity of urine samples to the Specific Gravity Index of the subject invention. The regression analysis statistics are also provided.

FIG. 10 illustrates the sensitivity of the SGI assay of the subject invention. The typical tests used for detecting a non-normal specific gravity, such as "dipsticks" that rely upon the amount of sodium, are usually not effective where the w/v of adulterant in a sample is below 10%. FIG. 9 demonstrates that embodiments of the subject invention are capable of detecting adulteration of only 5% w/v and even as little as 1% w/v, for the most common adulterants.

Sulfhydryl blocking adulterants such as iodoacetamide, at a concentration of 2 mM/L, have been shown to be effective in subversion of at least one of the most widely used EIA tests, but are detectable with the Specific Gravity Index assay of the subject invention. Cationic detergents are also being used to subvert standard assays. Cationic detergents are found in common over-the-counter eye drops, which have a concentration of about 0.05%, which is effective for subversion. The Specific Gravity Index assay is useful for detecting this type of subversion. As will be discussed below, both of these two new types of subversion can cause a Specific Gravity Index to fall below 1.003 and near that of water. Furthermore, the use of heavy metal adulteration, such as with cadmium acetate, copper sulfate, lead acetate, silver nitrate, mercuric chloride, chromium VI, and p-chloromercuribenzoate, at 2.0 mMol/L, can also lower the Specific Gravity Index to below 1.003 and near that of water.

As mentioned above, in one embodiment the reagent used in this SGI assay of the subject invention produces a yellow coloration to the urine sample being tested. More specifically, the cleavage of the o-nitrophenylgalactoside (o-NPG) into o-nitrophenol can produce a yellow coloration. The amount of coloration imparted to the sample is dependent upon the amount of sodium and potassium present in the sample to activate the β-galactosidase. Therefore, it is possible to utilize high urine:reagent ratio to ensure that the SGI for a sample is not inadvertently truncated due to insufficient reagent. In one embodiment, the sample:reagent ratio is between approximately 1:20 to approximately 1:100. In a more specific embodiment, the sample:reagent ratio is between approximately 1:50 and approximately 1:80.

Utilizing these percentages, the range for a normal SGI can be calculated as being between approximately 32 mEq/L and approximately 364 mEq/L. Thus, a combined Total Sodium and Potassium Value, which is the total amount of sodium and potassium in a urine sample, yielding a SGI below 32 mEq/L can be indicative of sample adulteration by dilution and a SGI over 364 mEq/L can be indicative of some other adulteration or substitution technique.

Specific gravity is a dimensionless quantity. As such, the mEq/L units of total sodium and potassium when converted gives a SGI of 0.003 for the 32 mEq/L low-end cut-off value reagent calibrator and a SGI of 0.035 for the 264 mEq/L high end cut-off value reagent calibrator. When measuring specific gravity, the decimal value is the specific gravity of a substance minus the specific gravity of $H_2O$, which should be 1.0000. Embodiments of the subject invention provide a Specific gravity Equivalent Value, based on the substituents of sodium and potassium in a urine sample, which can be calculated by adding 1 to the decimal value of the SGI. The currently recommended low specific gravity limit is 1.003 and the recommended high specific gravity limit is 1.035. Thus, for the purposes of automation and recording, it can be necessary to convert the SGI by adding 1.0 to the decimal value.

Alternatively, SGI can be calculated as the weight per unit volume of the non-aqueous constituents of a sample divided by the specific gravity of water, which is 1.0000 mg/mL. Thus, when the combined Total Sodium and Potassium Value is used, the SGI can range from between approximately 0.0030 and approximately 0.0350. A SGI below 0.0030 can be indicative of dilution of the sample and a SGI above 0.0350 can be indicative of adulteration.

As mentioned above, embodiments of the subject invention can be incorporated with automated laboratory equipment that is typically used for urine sample aliquot analysis. In one embodiment, the β-galactosidase and the o-NPG can be formulated as a single reagent, such that the reaction can be conducted as a single step. In an alternative embodiment, the β-galactosidase and the o-NPG can be formulated as separate reagents, such that the reaction is carried out in two or more steps.

Potassium chloride and sodium chloride, in the molar concentrations discussed above, can be formulated in an aqueous solution by a person of skill in the art to obtain an appropriate calibrator. In addition, 0.2% ProClin™ 300 can be used as a stabilizer for the aqueous calibrator. The stabilized calibrator can be used with automated machinery, such as clinical analyzers, to calibrate the high end cut-off value of 264 mEq/L and can be appropriately diluted to also calibrate the low end cut-off value of 32 mEq/L. Thus, a urine sample with an SGI above or below this range can be considered adulterated or tampered with in some manner.

One embodiment of the subject invention provides a liquid regent that can be added to a urine sample to initiate the yellow color change in the sample aliquot. The formulation for the reagent is prepared as follows:

| Reagent Concentrations: | |
|---|---|
| beta-Galactosidase | 25 to 8000 U/L |
| ortho-NPG | >0.2 mM |
| buffer | pH 7-9.5 |
| $Mg^{2+}$ | 0.01-10 mmol/L |
| EGTA (free acid) | 1-20 mmol/L |
| Serum Albumin | 0-5 g/L |
| N-Acetyl Cystine | 0.05-2M |
| ProClin 300 ® | 2 grams/L |

The ingredients should preferably be salt free, particularly with regard to heavy metals, calcium, sodium and potassium. It can also be desirable for pH adjustments to be made on aliquots of the reagent. Ideally, such aliquots are discarded in order to minimize potassium contamination of the reagent.

Urine typically contains calcium, which can vary between samples. Calcium can be a competitive inhibitor of the activation of beta-galactosidase by magnesium also present in the urine. Calcium is also unstable and can affect stability of the reagent. In one embodiment, EGTA is utilized in a reagent of the subject invention to complex calcium in the urine sample. The amount necessary will depend upon the amount of calcium that needs to be deactivated in a given sample. In the embodiment shown above, approximately 0.5-20 mmol/L are utilized. It is within the skill of person trained in the art to determine the appropriate amount of EGTA that may be required for a particular sample. Such variations that provide the same functionality, in substantially the same way, with substantially the same result are within the scope of this invention.

In an alternative embodiment, which can be useful in automation equipment, the ortho-nitrophenylgalactoside (o-NPG) can be provided as a second reagent of known concentration that can be added to the first regent to achieve the desired final concentration indicated above.

The stability of the o-NPG containing second reagent can be maximized by adjusting pH to be about 6.5. Ideally, a minimal amount of buffer is used to achieve this pH, so that when the second reagent is added to the first reagent, there is minimal or no effect on the final reaction pH, which should be about 8.5.

The addition of magnesium to the calibrators and controls in proportion to their concentration relative to mean normal Specific Gravity Index can improve sensitivity to the effect of dilution, or measurements at the lower cut-off value of 0.0030 SGI. In one embodiment, the amount of magnesium utilized in a reagent of the subject invention is between approximately 0.01 mmol/L to approximately 0.01-2 mmol/L. In a more particular embodiment, the amount of magnesium utilized in a reagent of the subject invention is between approximately 0.01 mmol/L to approximately 1 mmol/L.

Prior to analysis, the analyzer can be calibrated. This can be done with a reagent blank, a low end calibrator having a sodium and potassium concentration that is at or near the normal low range limit in human urine and the high end calibrator having a sodium and potassium concentration that is at or near the normal high range limit in human urine. In one embodiment, the low end calibrator contains approximately: 20 mEq/L of sodium chloride and 11.7 mEq/L of potassium chloride. In a further embodiment, the high end calibrator contains approximately 230 mEq/L of sodium chloride and 134 mEq/L of potassium chloride.

The measurement of creatinine levels in a urine sample is currently accepted as the gold standard for determining whether a sample has been diluted. Current government regulations mandate that the cut-off level for determining whether a sample has been diluted is 20 mg/dL. Thus, any sample presented that is measured with a creatinine level below 20 mg/dL is considered compromised by dilution.

Samples having a below-normal creatinine level can be further tested by measuring the specific gravity of the sample. Current tests for specific gravity are determined by measuring the uric acid levels in a sample and extrapolating a value from that measurement. If the specific gravity of a sample is measured to be below 1.0030, the sample is deemed as being abnormal or having been subjected to tampering.

Following are specifications for analyzing urine samples with several different types of automated equipment, including the Mindray BS-200 and the Beckman Coulter AU 400, AU 400e, AU 480, AU 640, AU640e and AU680 Series Clinical Chemistry Analyzers. The settings shown are intended to be guidelines for the indicated instruments. It is within the skill of a person trained in the art to recognize that such parameters will vary between instruments.

Assay Parameter Settings for Mindray BS-200 Analyzer

| Test: | SGI |
| --- | --- |
| No. | User Defined |
| Full Name: | Specific Gravity Index |
| Reaction Type: | Fixed-time |
| Pri. Wave | 405 nm |
| Sec Wave | 510 nm |
| Direction: | Increase |
| Reac. Time: | 0 and 9 |
| Incubation Time: | 3 |
| Unit: | g/mL |
| Precision: | 0.0001 |
| R1: | 250 |
| R2: | 100 |
| Sample Volume; | 4 |
| Compensate: Slope: 1 | Intercept: 1.0 |
| Calibration Parameters Rule | Logit-Log 5P |
| Replicates | 1 |
| Determination coeff. | 0 |

Calibrators: 0.0000 (deionized water), 0.0030 (low cut off for dilution), a mid-calibrator of 0.019, a high cut-off calibrator for salting of 0.0350, and a high range calibrator of 0.0500

Assay Parameter Settings for Beckman Coulter AU 400, AU 400e, AU 480, AU 640, AU640e and AU680 Series Clinical Chemistry Analyzers

| Reagent ID: | User defined | |
| --- | --- | --- |
| Test Name: | Specific Gravity Index | |
| Sample Volume: | 2 | |
| R1 Volume: | 107 | |
| R2 Volume: | 43 | |
| | Correlation factor | |
| | A 1.0 | B 1.0 |
| Wavelength: | Pri: 410 | Sec. 600 |
| Method: | FIXED | |
| Reaction Slope: | + | |
| Measuring Point 1: | First 11 | Last 26 |
| Measuring Point 2: | (Not Applicable) | |
| Calibration Type: CONC | 5AB Formula: | Polygonal Counts 1 |
| Point 1 H20 | 0.0000 | |
| Point 2 Low C/O | 0.0030 | |
| Point 3 MID | 0.0190 | |
| Point 4 Hi C/O | 0.0350 | |
| Point 5 Hi Range | 0.0500 | |

IV. Reagent System for Measurement of Creatinine in a Urine Sample

Most laboratories that conduct DOA urine tests currently perform creatinine assays as a means of detecting invalid samples. If the creatinine of a sample is measured below 20 mg/dL, procedures indicate that specific gravity tests should then be performed on the sample. Although measurement of creatinine has historically been the gold standard for the detection of subversion by dilution, new subversion techniques, such as in vivo dilution, are now being used to subvert detection. The technique of in vivo dilution was first discovered in studies of athletes and body builders who often take, a.k.a. "load", supplemental creatine to increase muscle mass. Creatine is converted in muscle to creatinine, which is subsequently excreted in the urine. [Schedel J, Tanaka M, Tanaka H, Kiyonaga M. et al. Consequences of one-week creatine supplementation on creatinine levels in athletes' serum and urine, Schweizerische Zeitschrift für <<Sportmedizin and Sporttraumatologie>> 2000; 48: 111-116.] Information can also be obtained from the World Wide Web about how to "load" with creatine and protein, consume large amounts of water prior to the test, and perform exercise to obtain both a normal urine creatinine and specific gravity while still diluting DOA below detection cut off levels.

Combatting efforts to subvert creatinine measurement start with improving the accuracy of creatinine assays. Aside from adulteration of a sample, there are other factors that can interfere with the accuracy of measuring urine creatinine. One of the factors is the presence of blood cells in urine. DOA such as cocaine, methamphetamines, opioids, benzodiazepines, synthetic marijuana, and others are toxic to the body. The DOA breakdown muscle tissue, including that in the kidneys, which results in increased amounts of blood cells in urine. Creatinine assays of urine samples utilize alkaline picrate to bind to creatinine imparting an orange coloration to the urine. The hemoglobin in blood cells, also being red, can interfere with the spectrophotometric measurement of creatinine in a urine sample.

Embodiments of the subject invention provide a reagent system for measuring creatinine in a urine sample that reduces the effect of blood cell hemoglobin when measuring creatinine in the urine. The reagent system can include two reagents. The first reagent can include potassium ferricyanide and a detergent, such as, for example, Teepol™. Potassium ferricyanide oxidizes the iron in hemoglobin to a ferric state forming methemoglobin. This can impart the reacted urine sample with a green color, which can be detected and measured spectrophotometrically at between about 500 nm and 570 nm, preferably at about 520 nm. This first spectrophotometric measurement can indicate the amount of hemoglobin that was in the sample.

In a further embodiment the reacted urine sample is treated with a second reagent of the reagent system that includes picric acid and sodium hydroxide with a chelating agent, such as, for example, ethyfenedianiinetetraacetic acid (EDTA). The further reacted sample can be spectrophotometrically analyzed a second time at between 590 nm and 620 nm, preferably about 600 nm. The first spectrophotometric measurement of the amount of hemoglobin in the sample can be subtracted from the second spectrophotometric measurement to provide a corrected spectrophotometric measure, which can be used to calculate a more accurate amount of the creatinine in the sample. Currently used protocols mandate that a creatinine value of less than 20 mg/dl indicates the sample is invalid.

Advantageously, embodiments of the reagent system for measuring creatinine can be used with automated equipment, such as clinical analyzers and laboratory equipment typically used to spectrophotometrically analyze a urine sample. One embodiment of a Reagent System of the subject invention for measurement of creatinine for use in automated equipment is described below:

| Reagent 1: | R1 | 1 Liter |
|---|---|---|
| To about 800 mL of deionized water add and mix: | | |
| | Tepol (Detergent) | 26.0 grams |
| | Potassium Ferricyanide | 0.094 grams |
| Mix to dissolve. Avoid excess exposure to light. | | |
| Adjust pH to pH 7.5 +/− 0.4 with 5% Potassium Hydroxide | | |
| Bring to 1 Liter total volume with deionized water and mix. Store refrigerated @ 2-8 Degrees Centigrade. | | |
| Reagent 2: | R2 | 1 Liter |
| To about 800 mL of deionized water add and mix: | | |
| | Sodium Hydroxide | 12.0 grams |
| | Di sodium EDTA | 0.14 grams |
| Acid | Picric | 2.0 grams |
| Bring to 1 Liter total volume with deionized water and mix. Store refrigerated at 2°-8° C. | | |

Following are specifications for analyzing urine samples with several different types of automated equipment, including the Beckman Coulter AU 400, AU 400e, AU 480, AU 640, AU640e and AU680 Series Clinical Chemistry Analyzers. The settings shown are intended to be guidelines for the indicated instruments. It is within the skill of a person trained in the art to recognize that such parameters will vary between instruments.

| Assay Parameter Settings | | | | |
|---|---|---|---|---|
| Specific Test Parameters 1 | | | | |
| Sample | Volume | 2 μL | | |
| | R1 Volume | 25 μL | | |
| | R2 Volume | 172 μL | | |
| Wavelength | Primary | 520 | Secondary | 600 |
| Method Fixed Reaction Slope + | | | | |
| Measuring Point 1 | First | 13 | Last | 17 |
| Specific Test Parameters 2 | | | | |
| | | L | H | |
| Normal Range | | 20 | 500 | |
| | | Unit mg/dL | Decimal Places 1 | |
| Calibration Specific Calibration Type 3AB Formula POLYNOMIAL Counts 2 | | | | |
| | conc | Factor-OD-L | Factor-OD-H | |
| Point 1 | 0 | −2.0 | 2.0 | |
| Point 2 | 100 | −2.0 | 2.0 | |
| Point 3 | 500 | −2.0 | 2.0 | |

V. Assay for Measuring pH of a Urine Sample

Current procedures mandate that urine samples submitted for DOA testing are considered invalid if the pH is below a 3.0 cut-off value or above a 10.0 cut-off value. Automated pH measurement using a mixture of pH indicator dyes has been used for several years in DOA testing. The reagents use a dye mixture producing a single color. However, these commonly used reagents suffer from limited ranges of detection and imprecision in the low pH range. Both of these may be attributed to the fact that the color development increases progressively from acid to alkaline pH levels. Thus, there are very low absorbance values at very low acid pH levels. Both the limited range of detection and the low sensitivity in the acid range limit the optimal detection of the common acid or alkali addition subversion means. A better range of measurement and more precise measurement in the acid range are required for optimal use in the diagnosis of SUD.

Figure 11:
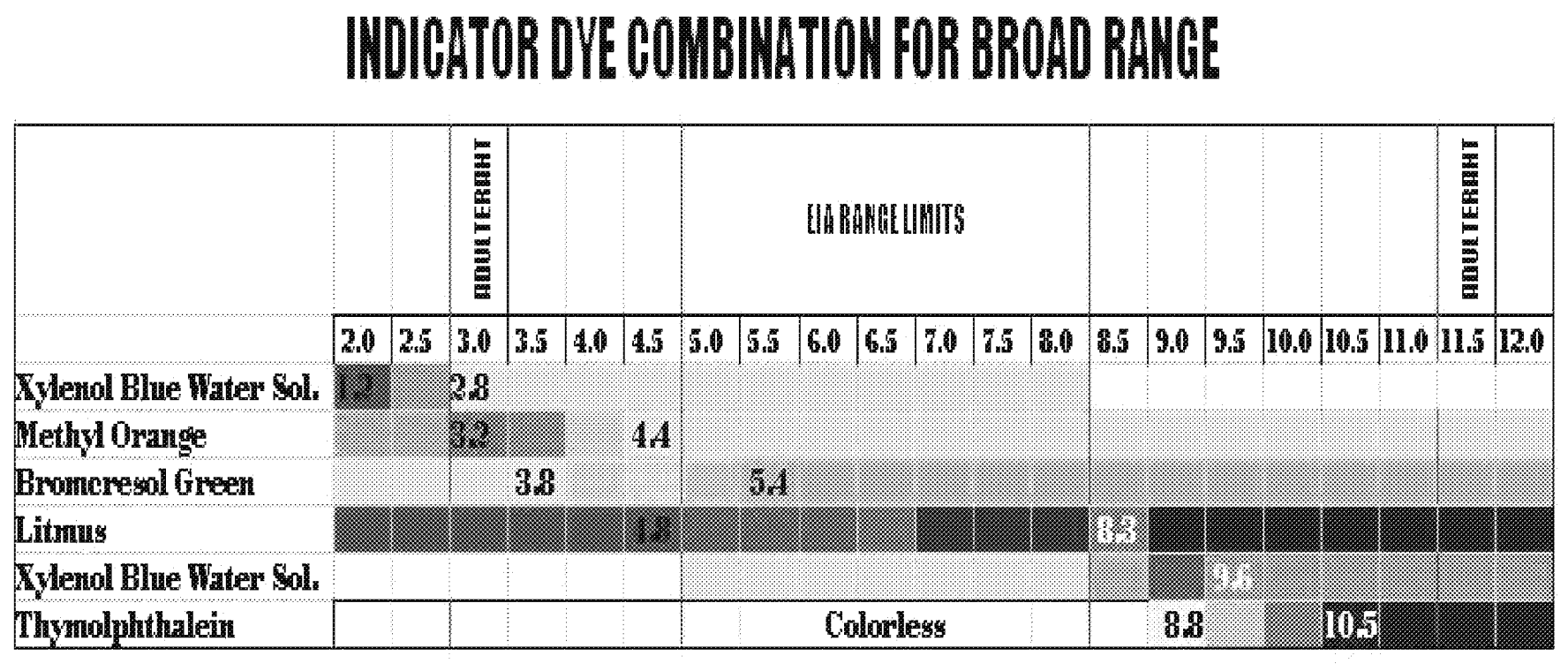

An improved, automated pH screening reagent and method have been developed for use as components of the SUD detection panel. The new reagent advantageously includes pH indicator dyes that form different colors in the acid and alkaline pH extremes. Colorimetric detection can be made using the bi-chromatic feature available on automated systems. The reagent uses indicator dyes that form a red color in the acid pH range (absorbance wavelength 510-520 nm) and other indicator dyes that form blue colors in the alkaline range (absorbance wavelength 590-610 nm). The 600 nm wavelength is used as a primary detection wavelength and the 510-520 wavelength is used as the secondary bi-chromatic wavelength. FIG. 11 shows the pH ranges and associated colors for the pH indicator dyes utilized with embodiments of the pH assay of the subject invention.

Bi-chromatic detection has been used on automated systems to correct for turbidity interference. The primary wavelength is used to detect the color formed by the reaction and the higher secondary wavelength is used to detect the absorbance of turbidity. The absorbance at the secondary wavelength is subtracted from the absorbance at the primary wavelength to correct for turbidity (Net Absorbance is Net absorbance=$(Abs_{Primary}-Abs_{Secondary})$. The bi-chromatic turbidity correction is a standard feature on virtually all clinical chemistry analyzers is use today.

Figure 12:
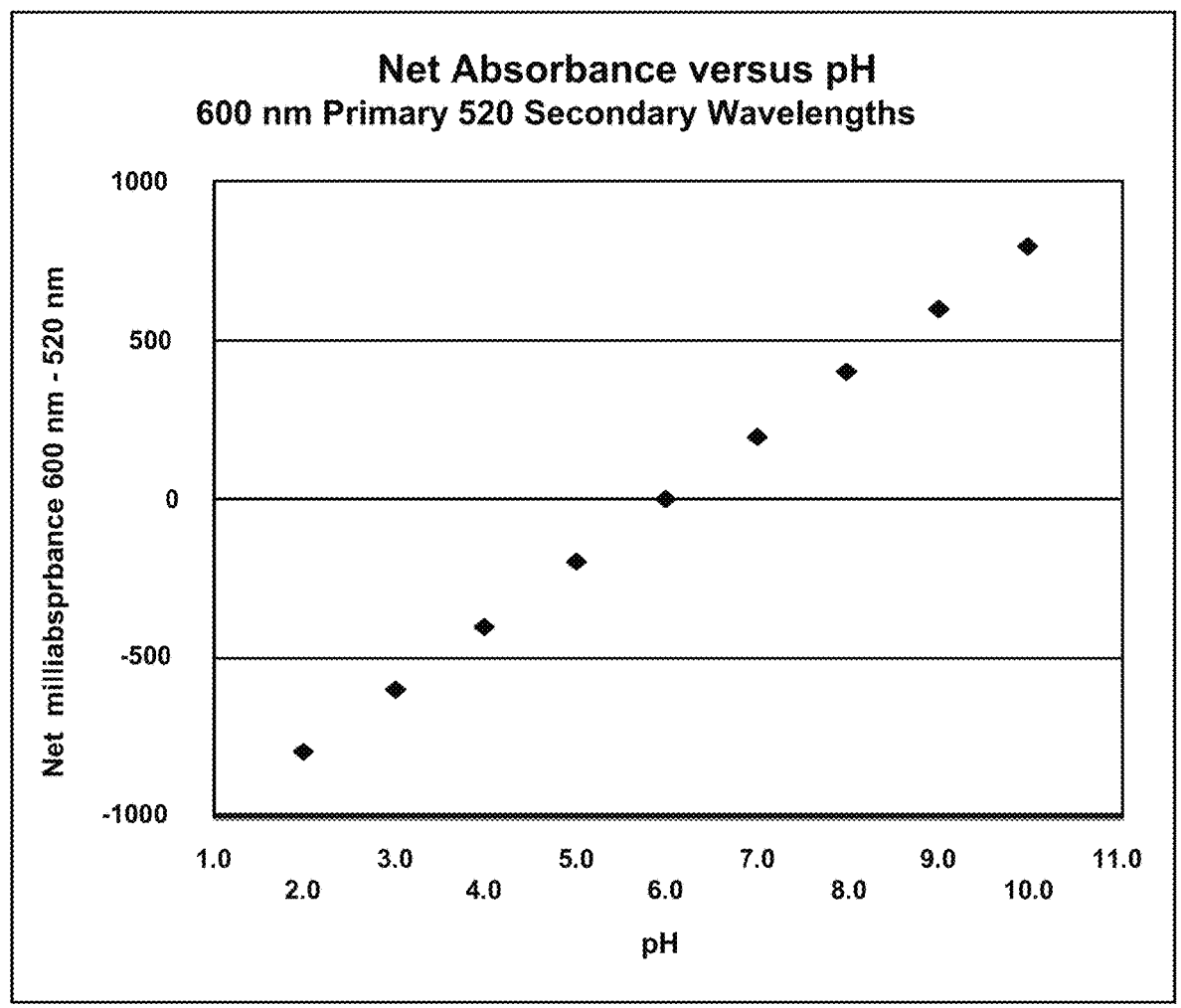
FIG. 12 is a graph related to the pH assay illustrating that a high absorbance at the primary wavelength and little absorbance at the secondary wavelength produces a high positive net absorbance.

Embodiments of the pH screening reagent and method of the subject invention uses the bi-chromatic turbidity correction arithmetic of the analyzers in a different method. Rather than correcting for turbidity, the effect of two different colors of dyes on a urine sample is measured. The extreme acid pH indicating dyes produce a highly negative net absorbance as the red colored dyes absorb at the secondary wavelength (510-520 nm) and no blue color is present, so that absorption at the primary wavelength is very low. At alkaline pH extremes, the color is blue and there is no red color present. Thus there is high absorbance at the primary wavelength and very little at the secondary wavelength thereby producing a high positive net absorbance. This is illustrated in the graph in FIG. 12.

The formulation for 1 liter of the reagent is as follows:
STEP A: To 60 mL of methanol containing 3 drops of 1 N NaOH add:
0.015 grams of Thymolphthalein
0.003 grams Xylenol Blue water soluble 0.005 grams Bromothymol Blue and Mix all ingredients to dissolve.

STEP B: To 700 mL deionized water add:
0.5 grams ProClin™ 300
0.004 grams Methyl Orange and mix to dissolve.
0.028 grams of Litmus STEP C: Add mixture from Step A and adjust pH to 7.4+/−0.1 with dilute sodium hydroxide or hydrochloric acid. Then bring to volume of 1 Liter with deionized water.

Calibrators having a buffered pH of 3.0 and 10.5 prepared by known means are used.

Following are specifications for analyzing urine samples utilizing Beckman Coulter automated equipment, including the AU 400, AU 400e, AU 480, AU 640, AU640e and AU680 Series Clinical Chemistry Analyzers. The settings shown are intended to be guidelines for the indicated instruments. It is within the skill of a person trained in the art to recognize that such parameters will vary between instruments.

| | |
|---|---|
| Sample Volume | 25 |
| R1 Volume | 150 |
| Wavelength Primary | 600 |
| Wavelength Secondary | 520 |
| Measuring Point 1 | First 0 Last 17 |
| Unit: pH Decimal Places: 1 Counts: 2 Process: OD | |
| Calibration Type A Formula Y = AX + B | |
| Point 1 CONC: 3.0 | |
| Point 2 CONC 10.5 | |

Substance Abuse and Mental Health Services Administration (SAMHSA) currently defines two principle means of detecting SUD: (a) interview and observation of behavior, and (b) by detection of efforts at subversion to hide or mask use of drugs-of-abuse (DOA). Of the two principle means, only the second one provides an objective result. There are twelve recognized subversion techniques. The embodiments of the subject invention provide a SUD Diagnostic Panel that includes six assays capable of detecting all twelve subversion techniques. This allows for more accurate validation of sample integrity before conducting further tests of DOA. It also provides an objective diagnosis of SUD.

The scope of the invention is not limited by the specific examples and suggested procedures and uses related herein since modifications can be made within such scope from the information provided by this specification to those skilled in the art.

All patents, patent applications, provisional applications, and other publications referred to or cited herein are incorporated by reference in their entirety, including all figures and tables, to the extent they are not inconsistent with the explicit teachings of this specification.

What is claimed is:

1. A method for diagnosing Substance Use Disorder (SUD), adapted for use with a urine sample, that comprises, analyzing the urine sample spectrophotometrically with a SUD Diagnostic Panel comprising:
an Oxidant History assay that utilizes a phosphotungstate reagent to measure uric acid in the sample and compare the amount of uric acid to a pre-determined value, such that an amount of uric acid below the pre-determined value indicates the urine sample is invalid;
a short-duration counterfeit urine assay that utilizes thymolphthalein monophosphate to detect the presence of an acid phosphatase marker in the urine sample, such that failure to detect the acid phosphatase marker indicates the sample is invalid;
a Specific Gravity Index assay that utilizes β-Galactosidase and o-nitrophenyl-galactoside to measure a combined amount of sodium and potassium in the urine sample to obtain a Specific Gravity Index value, such that a Specific Gravity Index value that is outside of a pre-determined range indicates the sample is invalid;
a creatinine assay that utilizes alkaline picrate to measure the amount of creatinine in the urine sample, such that an amount of creatinine outside of a pre-determined range indicates the sample is invalid; and
a pH assay that bi-chromatically measures pH of the urine sample, such that a pH in the acid range presents a different color than a pH in the alkaline range; and
determining if at least one of the assays of the SUD Diagnostic Panel indicates the urine sample is invalid, thereby providing an objective indication of SUD.

2. The method according to claim 1, wherein the Oxidant History reagent comprises a phosphotungstate.

3. The method according to claim 2, wherein the Oxidant History assay determines a historical presence of an oxidative-adulterant in a urine sample, by:
reacting the urine sample with a reagent comprising phosphotungstate;
analyzing the reacted urine sample using spectrophotometry to obtain a first light absorbance measurement of the reacted urine sample;
calculating a first Uric Acid Equivalents value utilizing the first light absorbance measurement;
analyzing the reacted urine sample again by spectrophotometry, after a pre-determined amount of time;
obtaining an additional light absorbance measurement of the reacted urine sample;
calculating an additional Uric Acid Equivalents value utilizing the additional light absorbance measurement;
utilizing the first Uric Acid Equivalents value and the additional Uric Acid Equivalents value to obtain an Oxidant History for the urine sample; and
analyzing the Oxidant History to determine whether the first Uric Acid Equivalent value is larger than the additional Uric Acid Equivalent value, which indicates the historical presence of an oxidative-adulterant in the urine sample.

4. The method according to claim 3, wherein analysis of the reacted sample is configured to be performed at a wavelength in a range between 580 nm and 800 nm.

5. The method according to claim 4, wherein any Uric Acid Equivalents value below 10 mg/dl is indicative of the urine sample being invalid.

6. The method according to claim 1, wherein the thymolphthalein monophosphate of the short-duration counterfeit urine assay catalyzes to a thymolphthalein chromogen.

7. The method according to claim 6, wherein the thymolphthalein chromogen formed by the short-duration counterfeit urine assay turns blue under alkaline pH conditions.

8. The method according to claim 7, wherein the short-duration assay comprises citric acid.

9. The method according to claim 8, wherein the short-duration assay further comprises an alkaline color developer reagent.

10. The method according to claim 1, further comprising conducting analysis of the urine sample with the SUD Diagnostic Panel prior to conducting analysis for drugs of abuse.

11. The method according to claim 10, further comprising conducting analysis of a retaken urine sample with the SUD Diagnostic Panel prior to conducting analysis for drugs of abuse.

12. The method according to claim 11, wherein a determination that the retaken sample is invalid is an objective indication of SUD.

13. The method according to claim 11, wherein a valid sample is analyzed for drugs of abuse utilizing liquid or gas chromatography/mass spectrometry procedures.

14. The method according to claim 13, wherein detection of drugs of abuse in the retaken sample is an objective indication of SUD.

15. The method according to claim 1, further comprising a long-duration counterfeit urine assay that utilizes p-nitrophenyl phosphate to detect the presence of an alkaline phosphatase marker in the urine sample, such that failure to detect the alkaline phosphatase marker indicates the sample is invalid.

16. The method according to claim 15, wherein the p-nitrophenyl phosphate catalyzes to a p-nitrophenol chromogen.

17. The method according to claim 15, wherein the assay has an alkaline pH.

18. The method according to claim 17, wherein the assay comprises zinc sulfate.

19. A method for measuring the amount of creatinine in a urine sample, utilizing a reagent system according to claim 8, comprising:
    reacting a urine sample with the first reagent, such that hemoglobin in the sample is converted to methemoglobin,
    obtaining a first spectrophotometric measurement of the sample,
    reacting the urine sample further with the second reagent;
    obtaining a second spectrophotometric measurement of the further reacted sample;
    subtracting the first spectrophotometric measurement from the second spectrophotometric measurement to obtain a corrected spectrophotometric measurement; and
    calculating an amount of creatinine in the sample utilizing the corrected spectrophotometric measurement.

20. The method according to claim 19, wherein the first reagent comprises potassium ferricyanide and the method further comprises spectrophotometrically analyzing the reacted urine sample at between 500 nm and 570 nm.

21. The method according to claim 20, further comprising spectrophotometrically analyzing the reacted urine sample at about 520 nm.

22. The method according to claim 19, wherein the second reagent comprises picric acid and sodium hydroxide that form a red color and the method further comprises spectrophotometrically analyzing the further reacted urine sample.

* * * * *

UNITED STATES PATENT AND TRADEMARK OFFICE
CERTIFICATE OF CORRECTION

| | |
|---|---|
| PATENT NO. | : 11,493,498 B2 |
| APPLICATION NO. | : 17/570413 |
| DATED | : November 8, 2022 |
| INVENTOR(S) | : Jerry W. Denney |

It is certified that error appears in the above-identified patent and that said Letters Patent is hereby corrected as shown below:

In the Specification

<u>Column 15,</u>
Line 27, "P-nitrophenyl" should read --P-nitrophenol--.

<u>Column 26,</u>
Line 55, "ethyfenedianiinetetraacetic" should read --ethylenediaminetetraacetic--.

<u>Column 27,</u>
Line 17,
"Di sodium EDTA    0.14 grams
Acid   Picric             2.0 grams" should read
--Disodium EDTA    0.14 grams
Picric Acid              2.0 grams--.

Signed and Sealed this
Twenty-sixth Day of December, 2023

*Katherine Kelly Vidal*
Katherine Kelly Vidal
*Director of the United States Patent and Trademark Office*